US010314925B2

(12) United States Patent
Salvatori et al.

(10) Patent No.: US 10,314,925 B2
(45) Date of Patent: Jun. 11, 2019

(54) THYMIDINE KINASE

(71) Applicant: MolMed SpA, Milan (IT)

(72) Inventors: Francesca Salvatori, Milan (IT); Stefania Massa, Milan (IT); Marina Radrizzani, Milan (IT); Salvatore Toma, Milan (IT)

(73) Assignee: MolMed SpA, Milan (IT)

( * ) Notice: Subject to any disclaimer, the term of this patent is extended or adjusted under 35 U.S.C. 154(b) by 0 days.

(21) Appl. No.: 16/192,224

(22) Filed: Nov. 15, 2018

(65) Prior Publication Data

US 2019/0070312 A1    Mar. 7, 2019

Related U.S. Application Data

(60) Continuation of application No. 14/676,696, filed on Apr. 1, 2015, now Pat. No. 10,155,052, which is a division of application No. 14/101,704, filed on Dec. 10, 2013, now Pat. No. 9,005,945, which is a division of application No. 13/601,174, filed on Aug. 31, 2012, now Pat. No. 8,642,311, which is a continuation of application No. 11/629,962, filed as application No. PCT/IB2005/002358 on Jun. 17, 2005, now Pat. No. 8,357,788.

(30) Foreign Application Priority Data

Jun. 18, 2004    (GB) .................................. 0413702.2

(51) Int. Cl.
*A61K 48/00* (2006.01)
*C12N 9/12* (2006.01)

(52) U.S. Cl.
CPC ........ *A61K 48/005* (2013.01); *A61K 48/0058* (2013.01); *C12N 9/1211* (2013.01)

(58) Field of Classification Search
None
See application file for complete search history.

(56) References Cited

U.S. PATENT DOCUMENTS

| | | | |
|---|---|---|---|
| 5,631,236 A | 5/1997 | Woo et al. | |
| 5,837,510 A | 11/1998 | Goldsmith et al. | |
| 5,861,290 A | 1/1999 | Goldsmith et al. | |
| 5,877,010 A | 3/1999 | Loeb et al. | |
| 6,074,836 A | 6/2000 | Bordignon et al. | |
| 8,357,788 B2 | 1/2013 | Radrizzani et al. | |
| 8,642,311 B2 | 2/2014 | Radrizzani et al. | |
| 9,005,945 B2 | 4/2015 | Salvatori et al. | |
| 2004/0166559 A1 | 8/2004 | Apperley et al. | |

FOREIGN PATENT DOCUMENTS

| | | |
|---|---|---|
| EP | 1 428 886 A1 | 6/2004 |
| FR | 2744731 A1 | 8/1997 |
| FR | 2751988 A1 | 2/1998 |
| WO | WO-90/07936 A1 | 7/1990 |
| WO | WO-95/14102 A1 | 5/1995 |
| WO | WO-95/30007 A1 | 11/1995 |
| WO | WO-97/29196 A1 | 8/1997 |
| WO | WO-97/37542 A1 | 10/1997 |
| WO | WO-98/04290 A2 | 2/1998 |
| WO | WO-99/19466 A2 | 4/1999 |
| WO | WO-01/79502 A2 | 10/2001 |

OTHER PUBLICATIONS

Baer, et al., "DNA Sequence and Expression of the B95-8 Epstein-Barr Virus Genome," *Nature* (London), vol. 310, pp. 207-213, 1984.
Binns, et al., "Comparison of a Conserved Region in Fowlpox Virus and Vaccinia Virus Genomes and the Translocation of the Fowlpox Virus Thymidine Kinase Gene," *J Gen. Virol*, vol. 69 pp. 1275-1283, 1988.
Boyle, et al., "Fowlpox Virus Thymidine Kinase: Nucleotide Sequence and Relationships to Other Thymidine Kinases," *Virology*, vol. 156, pp. 355 365, 1987.
Chalmers et al., "Elimination of the Truncated Message from the Herpes Simplex Virus Thymidine Kinase Suicide Gene," *Molecular Therapy*, vol. 4, pp. 146-148, 2001.
Davidson, et al., "The Complete DNA Sequence of Varicella-Zoster Virus," *J Gen. Virol.*, vol. 67, pp. 1759-1816, 1986.
Drinkwater, et al., "Chemically Induced Mutagenesis in a Shuttle Vector with a Low-Background Mutant Frequency," *PNAS*, vol. 83 pp. 3402-3406, 1986.
Esposito, et al., "Nucleotide Sequence of the Thymidine Kinase Gene Region of Monkeypox and Variola Viruses," *Virology*, vol. 135 pp. 561-567, 1984.
Fillat et al., "Suicide Gene Therapy Mediated by the Herpes Simplex Virus Thymidine Kinase Gene/Ganciclovir System: Fifteen Years of Application," *Current. Gene Therapy*, vol. 3, pp. 13-26, 2003.
Garin et al., "Molecular Mechanism for Ganciclovir Resistance in Human T Lymphocytes Transduced with Retroviral Vectors Carrying the Herpes simplex Virus Thymidine Kinase Gene," *Blood*, vol. 97, pp. 122-129, 2001.
Gershon, et al., "The Nucleotide Sequence Around the Capripoxvirus Thymidine Kinase Gene Reveals a Gene Shared Specifically with Leporipoxvirus," *J. Gen. Virol.*, vol. 70 pp. 525-533, 1989.
Honess, et al., "A Comparative Analysis of the Sequence of the Thymidine Kinase Gene of a Gammaherpesvirus, Herpesvirus Saimiri," *J Gen. Virol.*, vol. 70, pp. 3003-3013, 1989.
Horwitz, et al., "Selection of new Biological Activities from Random Nucleotide Sequences: Evolutionary and Practical Considerations," *Genome*, vol. 3 pp. 112-117, 1989.
Hruby, et al., "Fine Structure Analysis and Nucleotide Sequence of the Vaccinia Virus Thymidine Kinase Gene," *PNAS*, vol. 80 pp. 3411-3415, 1983.

(Continued)

*Primary Examiner* — Thaian N Ton
(74) *Attorney, Agent, or Firm* — Drinker Biddle & Reath LLP

(57) ABSTRACT

A polynucleotide comprising a nucleotide sequence encoding a thymidine kinase wherein at least one of the nucleotides corresponding to the splice donor site nucleotides is replaced by another nucleotide and wherein the nucleotides of the splice acceptor sites are not altered.

8 Claims, 14 Drawing Sheets

Specification includes a Sequence Listing.

(56) References Cited

OTHER PUBLICATIONS

Kilpatrick, et al., Cloning and Physical Mapping of Yaba Monkey Tumor virus DNA, *Virology*, vol. 143 pp. 399-406, 1985.
Kokoris, et al., "Enhancement of Tumor Ablation by a Selected HSV-1 Thymidine Kinase Mutant," *Gene Therapy*, vol. 6, pp. 1415-1426, 1999.
Lewis, et al., "Passage Through Mitosis is Required for Oncoretroviruses but not for the Human Immunodeficiency Virus," *J. Virol.*, vol. 68, pp. 510-516, 1994.
Lewis et al., "Human Immunodeficiency Virus Infection of Cells Arrested in the Cell Cycle," *EMBO. Journal*, vol. 11 pp. 3053-3058, 1992.
Liao, et al., "A Simple High=Efficiency Method for Random Mutagenesis of Cloned Genes Using Forced Nucleotide Misincorporation," *Gene*, vol. 88, pp. 107-111, 1990.
Lytvyn, et al., "Comparison of the Thymidine Kinase Genes from Three Entomopoxviruses," *J. Gen. Virol.*, vol. 73, pp. 3235-3240, 1992.
Marini, et al., "Assessment of Bystander Effect Potency Produced by Intratumoral Implantation of HSVtk-Expressing Cells Using Surrogate Marker Secretion to Monitor Tumor Growth Kinetics," *Gene Therapy*, vol. 2, pp. 655-659, 1995.
Martin, et al., "Genetic and Biochemical Characterization of the Thymidine Kinase Gene from Herpesvirus of Turkeys," *J. Virol.*, vol. 63, pp. 2847-2852, 1989.
McKnight, et al., "The Nucleotide Sequence and Transcript May of the Herpes Simplex Virus Thymidine Kinase Gene," *Nucl. Acids Res.*, vol. 8, pp. 5949-5964, 1980.
Meyer, et al., "Mapping of Deletions in the Genome of the Highly Attenuated Vaccinia Virus MVA and Their Influence on Virulence," *J Gen. Virol.*, vol. 72, pp. I031-1038, 1991.
Mittal, et al., "Analysis of the Bovine Herpesvirus Type 1 Thymidine Kinase (TK) Gene from Wild-Type Virus and TK-Deficient Mutants," *J. Virol.*, vol. 70, pp. 901-918, 1989.
Moolten, "Tumor Chemosensitivity Conferred by Inserted Herpes Thymidine Kinase Genes: Paradigm for a Prospective Cancer Control Strategy," *Cancer Res.*, vol. 46, pp. 5276-5284, 1986.
Moss, "Vaccinia Virus: A Tool for Research and Vaccine Development," *Science*, vol. 252, pp. 1662-1667, 1991.
Mullen, "Metabolic Suicide Genes in Gene Therapy," *Pharmac. Ther.*, vol. 63, pp. 199-207, 1994.
Nunberg, et al., "Identification of the Thymidine Kinase Gene of Feline Herpesvirus: Use of Degenerate Oligonucleotides in the Polymerase Chain Reaction to Isolate Herpesvirus Gene Homologs," *J Virol.*, vol. 63 pp. 3240-3249, 1989.
Otsuka, et al., "Nucleotide Sequence of the Marmoset Herpesvirus Thymidine Kinase Gene and Predicted Amino Acid Sequence of Thymidine Kinase Polypeptide," *Virology*, vol. 135, pp. 316-330, 1984.
Rettig, et al., "Transduction and Selection of Human T Cells with Novel CD34/Thymidine Kinase Chimeric Suicide Genes for the Treatment of Graft-Versus-Host Disease," *Molecular Therapy*, vol. 8, pp. 29-41, 2003.
Robertson, et al., "Evolution of the Herpes Thymidine Kinase: Identification and Comparison of the Equine Herpesvirus 1 Thymidine Kinase Gene Reveals Similarity to a Cell-Encoded Thymidylate Kinase," *Nuc. Acids Res.*, vol. 16 pp. 11303-11317, 1988.
Schnitzlein, et al., "A Rapid Method for Identifying the Thymidine Kinase Genes of Avipoxviruses," *J Virological Methods*, vol. 20 pp. 341-352, 1988.
Scott, et al., "Nucleotide and Predicted Amino Acid Sequences of the Marek's Disease Virus and Turkey Herpesvirus Thymidine Kinase Genes; Comparison with Thymidine Kinase Genes of Other Herpesviruses," *Journal of General Virology*, vol. 70 pp. 3055-3065, 1989.
Smith, et al., "Infectious Poxvirus Vectors Have Capacity for at Least 25000 Base Pairs of Foreign DNA," *Gene*, vol. 25, pp. 21-28, 1983.
Swain, et al., "Nucleotide Sequence of the Herpes Simplex Virus Type 2 Thymidine Kinase Gene," *Journal of Virology*, vol. 46, pp. 1045-1050, 1983.
Tiberghien, et al., "Administration of Herpes Simplex-Thymidine Kinase-Expressing donor T Cells with a T-Cell-Depleted Allogeneic Marrow Graft," *Blood*, vol. 97, pp. 63-72, 2001.
Upton, et al., "Identification and Nucleotide Sequence of the Thymidine Kinase Gene of Shope Fibroma virus," *Journal of Virology*, vol. 60 pp .920-927, 1986.
Verzeletti, "Herpes Simplex Virus Thymidine Kinase Gene Transfer for Controlled Graft-Versus-Host Disease and Graft-Versus-Leukemia: Clinical Follow-Up and Improved new Vectors," *Human Gene Therapy*, vol. 9, pp. 2243-2251, 1998.
Weir, et al., "Nucleotide Sequence of the Vaccinia Virus Thymidine Kinase Gene and the Nature of Spontaneous Frameshift Mutations," *Journal of Virology*, vol. pp. 46 530-537, 1983.
Fehse, et al., "A Novel 'Sort-Suicide' Fusion Gene Vector for T Cell Manipulation," *Gene Ther*. 9(23):1633-8, 2002.
Ebeling, et al., "Development and application of quantitative real time PCR and RT-PCR assays that discriminate between the full-length and truncated herpes simplex virus thymidine kinase gene," *J. Viol. Methods*, vol. 109, No. 2, pp. 177-186, 2003.
Hertel, "Combinatorial control of exon recognition," *J. Biol. Chem.*, vol. 283, No. 3, pp. 1211-1215, 2008.
Grantham, et al., "Codon frequencies in 119 individual genes confirm consistent choices of degenerate bases according to genome type," *Nucleic Acids Res.*, vol. 8, No. 9, pp. 1893-1912, 1980.
Blazar et al., "Advances in Graft-versus-Host Disease Biology and Therapy," *Nature Reviews*, 12: 443-458, 2012.

```
Tk wt     : 1    atggcttcgtacccctgccatcaacacgcgtctgcgttcgaccaggctgcgcgttctcgc 60
TkMut2    :      atggcttcgtacccctgccatcaacacgcgtctgcgttcgaccaggctgcgcgttctcgc
TkMut23   :      atggcttcgtacccctgccatcaacacgcgtctgcgttcgaccaggctgcgcgttctcgc
TkMut24   :      atggcttcgtacccctgccatcaacacgcgtctgcgttcgaccaggctgcgcgttctcgc
TkMut34   :      atggcttcgtacccctgccatcaacacgcgtctgcgttcgaccaggctgcgcgttctcgc
TkMut4    :      atggcttcgtacccctgccatcaacacgcgtctgcgttcgaccaggctgcgcgttctcgc
TkMut234  :      atggcttcgtacccctgccatcaacacgcgtctgcgttcgaccaggctgcgcgttctcgc Tk wt     : 61   ggccatagcaaccgacgtacggcgttgcgccctcgccggcagcaagaagccacggaagtc 120
TkMut2    :      ggccatagcaaccgacgtacggcgttgcgccctcgccggcagcaagaagccacggaagtc
TkMut23   :      ggccatagcaaccgacgtacggcgttgcgccctcgccggcagcaagaagccacggaagtc
TkMut24   :      ggccatagcaaccgacgtacggcgttgcgccctcgccggcagcaagaagccacggaagtc
TkMut34   :      ggccatagcaaccgacgtacggcgttgcgccctcgccggcagcaagaagccacggaagtc
TkMut4    :      ggccatagcaaccgacgtacggcgttgcgccctcgccggcagcaagaagccacggaagtc
TkMut234  :      ggccatagcaaccgacgtacggcgttgcgccctcgccggcagcaagaagccacggaagtc Tk wt     : 121  cgcctggagcagaaaatgcccacgctactgcgggtttatatagacggtcctcacgggatg 180
TkMut2    :      cgcctggagcagaaaatgcccacgctactgcgggtttatatagacggtcctcacgggatg
TkMut23   :      cgcctggagcagaaaatgcccacgctactgcgggtttatatagacggtcctcacgggatg
TkMut24   :      cgcctggagcagaaaatgcccacgctactgcgggtttatatagacggtcctcacgggatg
TkMut34   :      cgcctggagcagaaaatgcccacgctactgcgggtttatatagacggtcctcacgggatg
TkMut4    :      cgcctggagcagaaaatgcccacgctactgcgggtttatatagacggtcctcacgggatg
TkMut234  :      cgcctggagcagaaaatgcccacgctactgcgggtttatatagacggtcctcacgggatg Tk wt     : 181  gggaaaaccaccaccacgcaactgctggtggccctgggttcgcgcgacgatatcgtctac 240
TkMut2    :      gggaaaaccaccaccacgcaactgctggtggccctgggttcgcgcgacgatatcgtctac
TkMut23   :      gggaaaaccaccaccacgcaactgctggtggccctgggttcgcgcgacgatatcgtctac
TkMut24   :      gggaaaaccaccaccacgcaactgctggtggccctgggttcgcgcgacgatatcgtctac
TkMut34   :      gggaaaaccaccaccacgcaactgctggtggccctgggttcgcgcgacgatatcgtctac
TkMut4    :      gggaaaaccaccaccacgcaactgctggtggccctgggttcgcgcgacgatatcgtctac
TkMut234  :      gggaaaaccaccaccacgcaactgctggtggccctgggttcgcgcgacgatatcgtctac Tk wt     : 241  gtacccgagccgatgacttactggcaggtgctgggggcttccgagacaatcgcgaacatc 300
TkMut2    :      gtacccgagccgatgacttactggcaggtgctgggggcttccgagacaatcgcgaacatc
TkMut23   :      gtacccgagccgatgacttactggcaggtgctgggggcttccgagacaatcgcgaacatc
TkMut24   :      gtacccgagccgatgacttactggcaggtgctgggggcttccgagacaatcgcgaacatc
TkMut34   :      gtacccgagccgatgacttactggcaggtgctgggggcttccgagacaatcgcgaacatc
TkMut4    :      gtacccgagccgatgacttactggcaggtgctgggggcttccgagacaatcgcgaacatc
TkMut234  :      gtacccgagccgatgacttactggcaggtgctgggggcttccgagacaatcgcgaacatc
                                                                              2
Tk wt     : 301  tacaccacacaacacgcctcgaccagggtgagatatcggccggggacgcggcggtggta 360
TkMut2    :      tacaccacacaacacgcctcgaccagggcgagatatcggccggggacgcggcggtggta
TkMut23   :      tacaccacacaacacgcctcgaccagggcgagatatcggccggggacgcggcggtggta
TkMut24   :      tacaccacacaacacgcctcgaccagggcgagatatcggccggggacgcggcggtggta
TkMut34   :      tacaccacacaacacgcctcgaccagggtgagatatcggccggggacgcggcggtggta
TkMut4    :      tacaccacacaacacgcctcgaccagggtgagatatcggccggggacgcggcggtggta
TkMut234  :      tacaccacacaacacgcctcgaccagggcgagatatcggccggggacgcggcggtggta Tk wt     : 361  atgacaagcgcccagataacaatgggcatgccttatgccgtgaccgacgccgttctggct 420
TkMut2    :      atgacaagcgcccagataacaatgggcatgccttatgccgtgaccgacgccgttctggct
TkMut23   :      atgacaagcgcccagataacaatgggcatgccttatgccgtgaccgacgccgttctggct
TkMut24   :      atgacaagcgcccagataacaatgggcatgccttatgccgtgaccgacgccgttctggct
TkMut34   :      atgacaagcgcccagataacaatgggcatgccttatgccgtgaccgacgccgttctggct
TkMut4    :      atgacaagcgcccagataacaatgggcatgccttatgccgtgaccgacgccgttctggct
TkMut234  :      atgacaagcgcccagataacaatgggcatgccttatgccgtgaccgacgccgttctggct Tk wt     : 421  cctcatgtcgggggggaggctgggagttcacatgccccgccccggccctcaccctcatc 480
TkMut2    :      cctcatgtcgggggggaggctgggagttcacatgccccgccccggccctcaccctcatc
TkMut23   :      cctcatgtcgggggggaggctgggagttcacatgccccgccccggccctcaccctcatc
TkMut24   :      cctcatgtcgggggggaggctgggagttcacatgccccgccccggccctcaccctcatc
TkMut34   :      cctcatgtcgggggggaggctgggagttcacatgccccgccccggccctcaccctcatc
TkMut4    :      cctcatgtcgggggggaggctgggagttcacatgccccgccccggccctcaccctcatc
TkMut234  :      cctcatgtcgggggggaggctgggagttcacatgccccgccccggccctcaccctcatc
```

FIG. 1A

```
Tk wt     : 481  ttcgaccgccatcccatcgccgccctcctgtgctacccggccgcgcgataccttatgggc 540
TkMut2    :      ttcgaccgccatcccatcgccgccctcctgtgctacccggccgcgcgataccttatgggc
TkMut23   :      ttcgaccgccatcccatcgccgccctcctgtgctacccggccgcgcgataccttatgggc
TkMut24   :      ttcgaccgccatcccatcgccgccctcctgtgctacccggccgcgcgataccttatgggc
TkMut34   :      ttcgaccgccatcccatcgccgccctcctgtgctacccggccgcgcgataccttatgggc
TkMut4    :      ttcgaccgccatcccatcgccgccctcctgtgctacccggccgcgcgataccttatgggc
TkMut234  :      ttcgaccgccatcccatcgccgccctcctgtgctacccggccgcgcgataccttatgggc
                                 3        4
Tk wt     : 541  agcatgacccccaggccgtgctggcgttcgtggccctcatcccgccgaccttgcccgga 600
TkMut2    :      agcatgacccccaggccgtgctggcgttcgtggccctcatcccgccgaccttgcccgga
TkMut23   :      tccatgacccccaggccgtgctggcgttcgtggccctcatcccgccgaccttgcccgga
TkMut24   :      agcatgacccccaagccgtgctggcgttcgtggccctcatcccgccgaccttgcccgga
TkMut34   :      tccatgacccccaagccgtgctggcgttcgtggccctcatcccgccgaccttgcccgga
TkMut4    :      agcatgacccccaagccgtgctggcgttcgtggccctcatcccgccgaccttgcccgga
TkMut234  :      tccatgacccccaagccgtgctggcgttcgtggccctcatcccgccgaccttgcccgga Tk wt     : 601  acaaacatcgtgttgggggcccttccggaggacagacacatcgaccgcctggccaaacgc 660
TkMut2    :      acaaacatcgtgttgggggcccttccggaggacagacacatcgaccgcctggccaaacgc
TkMut23   :      acaaacatcgtgttgggggcccttccggaggacagacacatcgaccgcctggccaaacgc
TkMut24   :      acaaacatcgtgttgggggcccttccggaggacagacacatcgaccgcctggccaaacgc
TkMut34   :      acaaacatcgtgttgggggcccttccggaggacagacacatcgaccgcctggccaaacgc
TkMut4    :      acaaacatcgtgttgggggcccttccggaggacagacacatcgaccgcctggccaaacgc
TkMut234  :      acaaacatcgtgttgggggcccttccggaggacagacacatcgaccgcctggccaaacgc Tk wt     : 661  cagcgccccggcgagcggcttgacctggctatgctggccgcgattcgccgcgtttacggg 720
TkMut2    :      cagcgccccggcgagcggcttgacctggctatgctggccgcgattcgccgcgtttacggg
TkMut23   :      cagcgccccggcgagcggcttgacctggctatgctggccgcgattcgccgcgtttacggg
TkMut24   :      cagcgccccggcgagcggcttgacctggctatgctggccgcgattcgccgcgtttacggg
TkMut34   :      cagcgccccggcgagcggcttgacctggctatgctggccgcgattcgccgcgtttacggg
TkMut4    :      cagcgccccggcgagcggcttgacctggctatgctggccgcgattcgccgcgtttacggg
TkMut234  :      cagcgccccggcgagcggcttgacctggctatgctggccgcgattcgccgcgtttacggg Tk wt     : 721  ctgcttgccaatacggtgcggtatctgcagggcggcgggtcgtggtgggaggattgggga 780
TkMut2    :      ctgcttgccaatacggtgcggtatctgcagggcggcgggtcgtggtgggaggattgggga
TkMut23   :      ctgcttgccaatacggtgcggtatctgcagggcggcgggtcgtggtgggaggattgggga
TkMut24   :      ctgcttgccaatacggtgcggtatctgcagggcggcgggtcgtggtgggaggattgggga
TkMut34   :      ctgcttgccaatacggtgcggtatctgcagggcggcgggtcgtggtgggaggattgggga
TkMut4    :      ctgcttgccaatacggtgcggtatctgcagggcggcgggtcgtggtgggaggattgggga
TkMut234  :      ctgcttgccaatacggtgcggtatctgcagggcggcgggtcgtggtgggaggattgggga Tk wt     : 781  cagctttcggggacggccgtgccgccccagggtgccgagccccagagcaacgcgggccca 840
TkMut2    :      cagctttcggggacggccgtgccgccccagggtgccgagccccagagcaacgcgggccca
TkMut23   :      cagctttcggggacggccgtgccgccccagggtgccgagccccagagcaacgcgggccca
TkMut24   :      cagctttcggggacggccgtgccgccccagggtgccgagccccagagcaacgcgggccca
TkMut34   :      cagctttcggggacggccgtgccgccccagggtgccgagccccagagcaacgcgggccca
TkMut4    :      cagctttcggggacggccgtgccgccccagggtgccgagccccagagcaacgcgggccca
TkMut234  :      cagctttcggggacggccgtgccgccccagggtgccgagccccagagcaacgcgggccca Tk wt     : 841  cgaccccatatcggggacacgttatttaccctgtttcgggccccgagttgctggccccc 900
TkMut2    :      cgaccccatatcggggacacgttatttaccctgtttcgggccccgagttgctggccccc
TkMut23   :      cgaccccatatcggggacacgttatttaccctgtttcgggccccgagttgctggccccc
TkMut24   :      cgaccccatatcggggacacgttatttaccctgtttcgggccccgagttgctggccccc
TkMut34   :      cgaccccatatcggggacacgttatttaccctgtttcgggccccgagttgctggccccc
TkMut4    :      cgaccccatatcggggacacgttatttaccctgtttcgggccccgagttgctggccccc
TkMut234  :      cgaccccatatcggggacacgttatttaccctgtttcgggccccgagttgctggccccc Tk wt     : 901  aacggcgacctgtataacgtgtttgcctgggccttggacgtcttggccaaacgcctccgt 960
TkMut2    :      aacggcgacctgtataacgtgtttgcctgggccttggacgtcttggccaaacgcctccgt
TkMut23   :      aacggcgacctgtataacgtgtttgcctgggccttggacgtcttggccaaacgcctccgt
TkMut24   :      aacggcgacctgtataacgtgtttgcctgggccttggacgtcttggccaaacgcctccgt
TkMut34   :      aacggcgacctgtataacgtgtttgcctgggccttggacgtcttggccaaacgcctccgt
TkMut4    :      aacggcgacctgtataacgtgtttgcctgggccttggacgtcttggccaaacgcctccgt
TkMut234  :      aacggcgacctgtataacgtgtttgcctgggccttggacgtcttggccaaacgcctccgt
```

FIG. 1B

```
Tk wt    : 961  cccatgcacgtctttatcctggattacgaccaatcgcccgccggctgccgggacgccctg 1020
TkMut2   :      cccatgcacgtctttatcctggattacgaccaatcgcccgccggctgccgggacgccctg
TkMut23  :      cccatgcacgtctttatcctggattacgaccaatcgcccgccggctgccgggacgccctg
TkMut24  :      cccatgcacgtctttatcctggattacgaccaatcgcccgccggctgccgggacgccctg
TkMut34  :      cccatgcacgtctttatcctggattacgaccaatcgcccgccggctgccgggacgccctg
TkMut4   :      cccatgcacgtctttatcctggattacgaccaatcgcccgccggctgccgggacgccctg
TkMut234 :      cccatgcacgtctttatcctggattacgaccaatcgcccgccggctgccgggacgccctg Tk wt    : 1021 ctgcaacttacctccgggatggtccagacccacgtcaccacccccaggctccataccgacg 1080
TkMut2   :      ctgcaacttacctccgggatggtccagacccacgtcaccacccccaggctccataccgacg
TkMut23  :      ctgcaacttacctccgggatggtccagacccacgtcaccacccccaggctccataccgacg
TkMut24  :      ctgcaacttacctccgggatggtccagacccacgtcaccacccccaggctccataccgacg
TkMut34  :      ctgcaacttacctccgggatggtccagacccacgtcaccacccccaggctccataccgacg
TkMut4   :      ctgcaacttacctccgggatggtccagacccacgtcaccacccccaggctccataccgacg
TkMut234 :      ctgcaacttacctccgggatggtccagacccacgtcaccacccccaggctccataccgacg Tk wt    : 1081 atctgcgacctggcgcgcacgtttgcccgggagatgggggaggctaactga 1131
TkMut2   :      atctgcgacctggcgcgcacgtttgcccgggagatgggggaggctaactga
TkMut23  :      atctgcgacctggcgcgcacgtttgcccgggagatgggggaggctaactga
TkMut24  :      atctgcgacctggcgcgcacgtttgcccgggagatgggggaggctaactga
TkMut34  :      atctgcgacctggcgcgcacgtttgcccgggagatgggggaggctaactga
TkMut4   :      atctgcgacctggcgcgcacgtttgcccgggagatgggggaggctaactga
TkMut234 :      atctgcgacctggcgcgcacgtttgcccgggagatgggggaggctaactga
```

FIG. 1C

Splicing consensus sequence:

Donor     Intron     Acceptor

AG GUAAGU- - - - - - - - - -CAG G

FIG. 2

SFCMM-3

```
                                          donor site
Sbjct: 1981  ccgcctcgaccaa]ggtgagatatcggccggggacgcgcggtggtaatgacaagcgccca 2040
Sbjct: 2041  gataacaatgggcatgccttatgccgtgaccgacgccgttctggctcctcatgtcggggg 2100
Sbjct: 2101  ggaggctgggagttcacatgcccccccggccctcaccctcatcttcgaccgccatcc    2160
Sbjct: 2161  catcgccgccctcctgtgctaccggccgcgcgatacttatgggcagcatgacccccca    2220
             acceptor site
Sbjct: 2221  [g]gccgtgctggcgttcgtggcctcatcccgccgaccttgcccggcacaaacatcgtgtt 2280
```

TK3

```
             (donor site SFCMM-3/TK3)
Sbjct: 1981  ccgcctcgaccaa]gtgagatatcggccggggacgcgcggtggtaatgacaagcgccca  2040
Sbjct: 2041  gataacaatgggcatgccttatgccgtgaccgacgccgttctggctcctcatgtcggggg 2100
Sbjct: 2101  ggaggctgggagttcacatgcccccccggccctcaccctcatcttcgaccgccatcc    2160
                                                        acceptor site TK3
Sbjct: 2161  catcgccgccctcctgtgctaccggccgcgcgatacttatgggcagcatgacccccca    2220
             (acceptor site SFCMM-3)
Sbjct: 2221  [a]gccgtgctggcgttcgtggcctcatcccgccgaccttgcccggcacaaacatcgtgtt 2280
```

FIG. 5

Scheme of mutations introduced in the SFCMM-3 vector

```
Donor site                                              Acceptor site
  1   2                                                       3              4
  a   c                                                       tc             a
CTC GAC CAG GGT GAG --- --- --- --- --- --- --- ATG GGC AGC ATG ACC CCC CAG GCC
Leu asp gln gly glu --- --- --- --- --- --- --- met gly ser met thr pro gln ala
```

FIG. 6

THYMIDINE KINASE

CROSS-REFERENCE TO RELATED APPLICATIONS

This is a continuation of application Ser. No. 14/676,696, filed Apr. 1, 2015, which is a divisional of application Ser. No. 14/101,704, filed Dec. 10, 2013, now U.S. Pat. No. 9,005,945, which is a divisional of application Ser. No. 13/601,174, filed Aug. 31, 2012, now U.S. Pat. No. 8,642,311, which is a continuation of application Ser. No. 11/629,962, filed Sep. 3, 2008, now U.S. Pat. No. 8,357,788, which is the National Stage of International Application No. PCT/IB05/02358, filed on Jun. 17, 2005, which claims priority under 35 U.S.C. § 119(a) to GB Application No. 0413702.2, filed Jun. 18, 2004, each of which is hereby incorporated herein by reference in its entirety.

SEQUENCE LISTING

The instant application contains a Sequence Listing which has been submitted ASCII format via EFS-Web and is hereby incorporated by reference in its entirety. Said ASCII copy, created on Nov. 1, 2018, is named 048974_0001_04_583538_ST25, and is 17,756 bytes in size.

FIELD OF THE INVENTION

The present invention relates to a nucleic acid encoding a substantially non-splicing thymidine kinase gene and its use in therapy.

BACKGROUND TO THE INVENTION

There is considerable interest in the use of metabolic suicide genes in gene therapy. Numerous suicide genes are described in the literature, such as, for example, the genes coding for cytosine deaminase, purine nucleoside phosphorylase or a thymidine kinase. Among these genes, the gene coding for herpes simplex virus type 1 thymidine kinase (HSV-tk) is especially advantageous from a therapeutic standpoint. The HSV-tk gene expresses an enzyme, which when used in combination with the nucleoside analogue ganciclovir, is capable of specifically eliminating dividing cells. Of particular importance is the presence of a propagated toxicity effect ("bystander" effect) which is associated with the use of HSV-tk/ganciclovir. This effect manifests itself in the destruction not only of the cells which have incorporated the thymidine kinase (tk) gene, but also the neighbouring cells.

The mechanism of action of the HSV-tk/ganciclovir system, may be outlined as follows: mammalian cells modified to express the TK enzyme implement the first step of phosphorylation of ganciclovir to yield ganciclovir monophosphate. Subsequently, cellular kinases enable this ganciclovir monophosphate to be metabolised successively to diphosphate and then triphosphate. The ganciclovir triphosphate thus generated then produces toxic effects by becoming incorporated in the DNA, and partially inhibits the cellular DNA polymerase alpha, thereby causing DNA synthesis to be stopped and hence leading to cell death (Moolten, 1986; Mullen, 1994).

The HSV-tk/ganciclovir system can be used in a large number of therapeutic applications and numerous clinical trials have been implemented in the last decade.

Methods of using the HSV-tk gene in gene therapy are disclosed in, for example, WO90/07936, U.S. Pat. Nos. 5,837,510, 5,861,290, WO 98/04290, WO 97/37542 and U.S. Pat. No. 5,631,236.

One interesting application of the HSV-tk/ganciclovir system is in the prevention of graft-versus-host disease (GvHD), a condition that can interfere with the outcome of allogeneic bone marrow transplantation, the treatment of choice for many hematological malignancies. GvHD occurs when T-cells in the transplanted stem cell graft begin to attack the recipient's body. Removal of T-cells from the graft may prevent GvHD but also favours disease recurrence and graft rejection. To counter these effects, allogeneic bone marrow transplant patients can be treated by introducing donor T lymphocytes after a delay following the allogeneic bone marrow transplant. Transferring the HSV-tk gene to donor T lymphocytes allows their eradication after ganciclovir administration in case of the emergence of GvHD. In one trial, patients received a T-cell depleted bone marrow transplantation together with increasing doses of donor lymphocytes transduced with the HSV-tk gene (Tiberghien et al., 2001). Circulating HSV-tk-expressing cells could be detected for more than one year after engraftment in all patients. Six out of the twelve patients developed GvHD and received ganciclovir, substantially reducing the number of circulating modified cells (85% average decrease in absolute number).

Mutants in the HSV-tk gene have been made which increase its biological activity. Examples of such mutant HSV-tk genes are described in, for example, Kokoris et al (1999), WO 95/30007, U.S. Pat. No. 5,877,010, WO 99/19466 and WO 95/14102. However, a serious problem associated with the thymidine kinase/ganciclovir system is the emergence of ganciclovir resistance in HSV-tk transduced cells. This is of particular importance, since the relative proportion of cells which are resistant to ganciclovir may rapidly increase through the course of treatment.

The presence of ganciclovir resistance in a lymphoblastoid human T-cell line transduced with a retroviral vector containing the HSV-tk gene was found to be associated with a 227 base pair deletion in the HSV-tk gene (Fillat et al., 2003). The same deletion was also present in human primary T cells transduced with the vector and in 12 patients who received transduced donor T cells (Garin et at, 2001). WO 01/79502 discloses that the cause of this deletion is believed to be due to the presence of nucleotide sequences in the HSV-tk mRNA which act as splice sites to cause the production of a proportion of virus particles carrying an aberrant form of the gene, the remainder carrying the full length gene. A mutant of the thymidine kinase gene is disclosed in WO 01/79502 and in Chalmers 2001, Molecular Therapy 4:146-148, in which the splice sites are removed, and which reduces the production of the aberrant form of the thymidine kinase gene. However, this mutant is still associated with a detrimental amount of gene splicing. CD34-tk fusion constructs are disclosed in Rettig et al., 2003. These fusion constructs contain modified HSV-tk genes. However, there is no demonstration that the modified genes reduce splicing of the HSV-tk mRNA.

Thus, there remains a need for a modified thymidine kinase gene that is not susceptible to gene splicing and which addresses the problems associated with ganciclovir resistance.

SUMMARY OF THE INVENTION

The present invention overcomes the aforementioned problem by providing a HSV-tk gene that expresses a greater proportion of unspliced mRNA over previously disclosed HSV-tk genes. We have identified a splice acceptor site 14 base pairs upstream of the previously identified acceptor site. We show that previous attempts to inhibit splicing by modification of the previously identified donor and acceptor sites can result in activation of this acceptor site and subsequent gene splicing. We surprisingly demonstrate that the modification of the HSV-tk gene at certain specific nucleotides provides a HSV-tk gene that is capable of expressing substantially splice-free mRNA. In particular, we show that mutating at least one of the nucleotides at the splice donor site can substantially prevent splicing.

STATEMENTS OF THE INVENTION

According to a first aspect of the present invention there is provided a polynucleotide comprising a nucleotide sequence encoding a thymidine kinase wherein at least one of the nucleotides corresponding to splice donor site nucleotides is replaced by another nucleotide and wherein the nucleotides of the splice acceptor sites are not altered.

Preferably, at least one of the nucleotides corresponding to splice donor site nucleotides at positions 329 and 330 of the wild type sequence in FIGS. 1A-1C (Tk wt) is replaced by another nucleotide and wherein the nucleotides of the splice acceptor sites are not altered.

In one embodiment, the nucleotide at position 330 is changed from T to C.

According to a second aspect of the present invention there is provided a polynucleotide comprising a nucleotide sequence encoding a thymidine kinase wherein at least one of the nucleotides corresponding to splice donor site nucleotides at positions 329 and 330 of the wild type sequence in FIGS. 1A-1C (Tk wt) is replaced by another nucleotide and wherein the nucleotides of the splice acceptor sites are not altered.

In one embodiment both the nucleotides corresponding to splice donor site nucleotides at positions 329 and 330 of the wild type sequence in FIGS. 1A-1C are replaced by another nucleotide.

In one embodiment the nucleotide at position 330 is changed from T to C.

According to a third aspect of the present invention there is provided a polynucleotide comprising a nucleotide sequence encoding a thymidine kinase wherein at least one of the nucleotides corresponding to the splice donor site nucleotides at positions 329 and 330 of the wide type sequence in FIGS. 1A-1C (Tk wt) is replaced by another nucleotide and wherein at least one of the nucleotides corresponding to splice acceptor site nucleotides at positions 554 and 555 and at least one of the nucleotides corresponding to splice acceptor site nucleotides at positions 662 and 663 of the wild type sequence in FIGS. 1A-1C is not altered.

Preferably both the nucleotides corresponding to positions 554 and 555 are not altered.

Preferably both the nucleotides corresponding to positions 662 and 663 are not altered.

In one embodiment both the nucleotides corresponding to splice donor site nucleotides at positions 329 and 330 of the wild type sequence in FIGS. 1A-1C are replaced by another nucleotide.

In one embodiment the nucleotide at position 330 is changed from T to C.

According to a fourth aspect of the present invention there is provided a polynucleotide comprising the TkMut2 sequence in FIGS. 1A-1C.

According to a fifth aspect of the present invention there is provided a polynucleotide comprising a nucleotide sequence encoding a thymidine kinase wherein at least one of the splice acceptor nucleotides corresponding to the nucleotide(s) at positions 329 and 330 of the wild type sequence in FIGS. 1A-1C (Tk wt) is replaced by another nucleotide and wherein at least one of the nucleotides corresponding to the splice acceptor site nucleotides at positions 541 and 542 of the wild type sequence in FIGS. 1A-1C is replaced by another nucleotide.

In one embodiment both the nucleotides corresponding to splice donor site nucleotides at positions 329 and 330 of the wild type sequence in FIGS. 1A-1C are replaced by, another nucleotide.

In one embodiment the nucleotide corresponding to position 330 is changed from T to C.

In another embodiment both the nucleotides corresponding to splice acceptor site nucleotides at positions 541 and 542 of the wild type sequence in FIGS. 1A-1C are replaced by another nucleotide.

In another embodiment the nucleotide corresponding to the nucleotide at positions 541 is changed from A to T.

In another embodiment the nucleotide corresponding to the nucleotide at position 542 is changed from G to C.

In another embodiment at least one of the nucleotides corresponding to the splice acceptor site nucleotides at position 554 and 555 of the wild type sequence in FIGS. 1A-1C are replaced by another nucleotide such that there is no splice site present.

In one embodiment both the nucleotides corresponding to splice acceptor site nucleotides at positions 541 and 542 of the wild type sequence in FIGS. 1A-1C are replaced by another nucleotide such that there is no splice site present.

In another embodiment the nucleotide corresponding to the nucleotide at position 555 is changed from G to A.

According to a sixth aspect of the present invention there is provided a polynucleotide comprising the TkMut23 sequence in FIGS. 1A-1C.

According to a seventh aspect of the present invention there is provided a polynucleotide comprising the TkMut234 sequence in FIGS. 1A-1C.

According to an eighth aspect of the present invention there is provided a polynucleotide comprising a nucleotide sequence encoding a thymidine kinase wherein at least one of the splice acceptor site nucleotides corresponding to the nucleotide(s) at positions 329 and 330 of the wild type sequence in FIGS. 1A-1C (Tk wt) is replaced by another nucleotide and wherein the nucleotides corresponding to the splice acceptor site nucleotides at positions 554 and 555 of the wild type sequence in FIGS. 1A-1C is replaced by another nucleotide.

In one embodiment both the nucleotides corresponding to splice donor site nucleotides at positions 329 and 330 of the wild type sequence in FIGS. 1A-1C are replaced by another nucleotide.

In another embodiment both the nucleotides corresponding to splice acceptor site nucleotides at positions 554 and 555 of the wild type sequence in FIGS. 1A-1C are replaced by another nucleotide.

Preferably the nucleotide corresponding to the nucleotide at position 330 is changed from T to C.

Preferably the nucleotide corresponding to the nucleotide at position 555 is changed from G to A.

According to a ninth aspect of the present invention there is provided a polynucleotide comprising the Tk-Mut24 sequence in FIGS. 1A-1C.

According to a tenth aspect of the present invention there is provided a polynucleotide comprising a nucleotide sequence encoding a thymidine kinase wherein at least one of the nucleotides corresponding to splice acceptor site nucleotides at position 554 and 555 of the wild type sequence in FIGS. 1A-1C (Tk wt) is replaced by another nucleotide.

In one embodiment both the nucleotides corresponding to splice donor site nucleotides at positions 554 and 555 of the wild type sequence in FIGS. 1A-1C are replaced by another nucleotide.

In one embodiment the nucleotide corresponding to the nucleotide at position 555 is changed from G to A.

In one embodiment at least one of the splice acceptor site nucleotides corresponding to the nucleotides at positions 541 and 542 of the wild type sequence in FIGS. 1A-1C is also replaced by another nucleotide such that there is no splice site present.

In another embodiment both the nucleotides corresponding to splice acceptor site nucleotides at positions 541 and 542 of the wild type sequence in FIGS. 1A-1C are also replaced by another nucleotide such that there is no splice site present.

In another embodiment the nucleotide corresponding to the nucleotide at position 541 is changed from A to T.

In another embodiment the nucleotide corresponding to the nucleotide at position 542 is changed from G to C.

According to an eleventh aspect of the present invention there is provided a polynucleotide comprising the TkMut4 sequence in FIGS. 1A-1C.

According to a twelfth aspect of the present invention there is provided a polynucleotide comprising the TkMut34 sequence in FIGS. 1A-1C.

Preferably the replacement nucleotide does not alter the sequence of the polypeptide encoded by said nucleotide sequence.

According to a thirteenth aspect of the present invention there is provided a vector comprising a polynucleotide of the present invention.

Preferably, the vector is an expression vector.

According to a fourteenth aspect of the present invention there is provided a host cell comprising a polynucleotide or a vector the present invention.

According to a fifteenth aspect of the present invention there is provided a pharmaceutical composition comprising a polynucleotide, a vector or a host cell of the present invention, and a pharmaceutically acceptable carrier.

According to a sixteenth aspect of the present invention there is provided a kit comprising
  (i) a polynucleotide, a vector, a host cell or a pharmaceutical composition of the present invention; and
  (i) a substantially non-toxic agent which is converted by thymidine kinase into a toxic agent.

According to a seventeenth aspect of the present invention there is provided a polynucleotide, a vector, a host cell or a pharmaceutical composition of the present invention for use in medicine.

According to an eighteenth aspect of the present invention there is provided products containing a polynucleotide, a vector, a host cell or a pharmaceutical composition of the present invention, and a substantially non-toxic agent for simultaneous, separate or sequential use in treating a patient with cells in need of destruction, wherein said substantially non-toxic agent is converted by thymidine kinase to a toxic agent.

According to a nineteenth aspect of the present invention there is provided a method of destroying cells comprising (i) introducing into said cells a polynucleotide or a vector of the present invention; and
  (ii) simultaneously, separately or sequentially contacting said cells with a substantially non-toxic agent which is converted by thymidine kinase to a toxic agent.

According to a twentieth aspect of the present invention there is provided a method of destroying cells comprising
  (i) introducing into said cells a polynucleotide or a vector of the present invention;
  (ii) allowing said cells to express thymidine kinase; and
  (ii) contacting said cells with a substantially non-toxic agent which is converted by thymidine kinase to a toxic agent.

According to a twenty first aspect of the present invention there is provided a method of treating a patient with cells in need of destruction comprising
  (i) introducing into the patient a polynucleotide, a vector or a pharmaceutical composition of the present invention;
  (ii) simultaneously, separately or sequentially introducing into the patient a substantially non-toxic agent which is converted by thymidine kinase to a toxic agent.

According to a twenty second aspect of the present invention there is provided a method of treating a patient with cells in need of destruction comprising
  (i) introducing into the patient a polynucleotide, a vector or a pharmaceutical composition of the present invention;
  (ii) allowing said polynucleotide or vector to be taken up by said cells;
  (iii) allowing said cells to express thymidine kinase; and
  (iv) introducing into the patient a substantially non-toxic agent which is converted by thymidine kinase to a toxic agent.

According to a twenty third aspect of the present invention there is provided a method of treating a patient with cells in need of destruction comprising
  (i) removing the cells from the patient or donor cells;
  (ii) introducing into the cells ex vivo a polynucleotide or a vector of the present invention;
  (iii) introducing the modified cells into the patient;
  (iv) allowing the cells to express thymidine kinase; and
  (v) administering to the patient a substantially non-toxic agent which is converted by thymidine kinase into a toxic agent.

According to a twenty fourth aspect of the present invention there is provided a method of preventing graft-versus-host disease in a patient comprising:
  (i) administering to a host T-cells genetically engineered to include a polynucleotide of the present invention or a vector of the present invention; and
  (ii) administering to said host, prior to the occurrence of graft-versus-host disease, a substantially non-toxic agent in an amount effective to kill said genetically engineered T-cells through interaction of said agent with thymidine kinase.

Preferably the substantially non-toxic agent used in the present invention is any one of ganciclovir, acyclovir, triflurothymidine, 1-[2-deoxy, 2-fluoro, β-D-arabino furanosyl]-5-iodouracil, ara-A, ara 1, 1-β-D arabino furanosyl thymine, 5-ethyl-2'deoxyurine, 5-iodo-5'-amino-2, 5'-dideoxyuridine, idoxuridine, AZT, AIV, dideoxycytidine, Ara C and bromovinyl deoxyuridine (BVDU).

According to a twenty fifth aspect of the present invention there is provided use of a polynucleotide, a vector or a host cell of the present invention in the preparation of a medicament for destroying cells in a patient.

According to a twenty sixth aspect of the present invention use of polynucleotide, vector or a host cell of the present invention in the preparation of a medicament for the treatment of cancer.

DETAILED DESCRIPTION

Various preferred features and embodiments of the present invention will now be described by way of non-limiting examples.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, 3. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; and E. M. Shevach and W. Strober, 1992 and periodic supplements, *Current Protocols in Immunology*, John Wiley & Sons, New York, N.Y. Each of these general texts is herein incorporated by reference.

HSV-tk Gene

As used herein, the term "not altered" means not altered from the wild type sequence (Tk wt).

As used herein, the term "replaced by another nucleotide" means replaced by a nucleotide that differs from the wild type sequence (Tk wt). The replacements are made such that the relevant splice donor site or splice acceptor sites are removed.

Thymidine kinase mutants of the present invention may be prepared from a wide variety of thymidine kinases. Preferably, the thymidine kinase mutant is derived from Herpesviridae thymidine kinase including for example both primate herpesviruses, and nonprimate herpesviruses such as avian herpesviruses. Representative examples of suitable herpesviruses include Herpes Simplex Virus Type 1 (McKnight et al., 1980), Herpes Simplex Virus Type 2 (Swain and Galloway, 1983), Varicella Zoster Virus (Davidson and Scott, 1986), marmoset herpesvirus (Otsuka and Kit, 1984), feline herpesvirus type 1 (Nunberg et al., 1989), pseudorabies virus (Kit and Kit, U.S. Pat. No. 4,514,497, 1985), equine herpesvirus type 1 (Robertson and Whalley, 1988), bovine herpesvirus type 1 (Mittal and Field, 1989), turkey herpesvirus (Martin et al., 1989), Marek's disease virus (Scott et al., 1989), herpesvirus saimiri (Honess et al., 1989) and Epstein-Barr virus (Baer et al., 1984).

Such herpesviruses may be readily obtained from commercial sources such as the American Type Culture Collection ("ATCC", Rockville, Md.). Deposits of certain of the above-identified herpesviruses may be readily obtained from the ATCC, for example: ATCC No. VR-539 (Herpes Simplex type 1); ATCC Nos. VR-734 and VR-540 (Herpes Simplex type 2); ATCC No. VR-586 (Varicella Zoster Virus); ATCC No. VR-783 (Infectious laryngothracheitis); ATCC Nos. VR-624, VR-987, VR-2103, VR-2001, VR-2002, VR-2175, VR-585 (Marek's disease virus); ATCC Nos. VR-584B and VR-584B (turkey herpesvirus); ATCC Nos. VR-631 and VR-842 (bovine herpesvirus type 1); and ATCC Nos. VR-2003, VR-2229 and VR-700 (equine herpesvirus type 1). Herpesviruses may also be readily isolated and identified from naturally occurring sources (e.g., from an infected animal).

The thymidine kinase gene may be readily isolated and mutated as described below, in order to construct nucleic acid molecules encoding a thymidine kinase gene comprising one or more mutations which substantially reduce the splicing of the gene, as compared to unmutated thymidine kinase. As utilized herein, it should be understood that "unmutated thymidine kinase" refers to native or wild-type thymidine kinase such as that described by McKnight et al. (*Nucl. Acids Res.* 8:5949-5964, 1980).

It should be noted that in this application nucleotide positions are referred to by reference to a position in FIGS. 1A-1C. However, when such references are made, it will be understood that the invention is not to be limited to the exact sequence as set out in the figure but includes variants and derivatives thereof. Thus, identification of nucleotide locations in other thymidine kinase sequences are contemplated (i.e., nucleotides at positions which the skilled person would consider correspond to the positions identified in FIGS. 1A-1C). The person skilled in the art can readily align similar sequences and locate the same nucleotide locations.

Construction of HSV-tk Mutants

Thymidine kinase mutants of the present invention may be constructed using a variety of techniques. For example, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codon altered according to the substitution, deletion, or insertion required. Deletion or truncation derivatives of thymidine kinase mutants may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (*Molecular cloning: A Laboratory Manual*, 2d Ed., Cold Spring Harbor Laboratory Press, 1989).

Thymidine kinase mutants may also be constructed utilizing techniques of PCR mutagenesis, chemical mutagenesis, chemical mutagenesis (Drinkwater and Klinedinst, 1986) by forced nucleotide misincorporation (e.g., Liao and Wise, 1990), or by use of randomly mutagenized oligonucleotides (Horwitz et al., 1989).

In a preferred embodiment of the present invention, the nucleotides are modified taking note of the genetic code such that a codon is changed to a degenerate codon which codes fir the same amino acid residue. In this way, it is possible to make coding regions of the protein of interest which encode wild type protein but which do not contain a functional splice site.

Splice Sites

The proportion of RNA which is removed (or "spliced out") during splicing is typically called an intron, and the two pieces of RNA either side of the intron that are joined by splicing are typically called exons (FIG. 2).

A splice donor site is a site in RNA which lies at the 5' side of the RNA which is removed during the splicing process and which contains the site which is cut and rejoined to a nucleotide residue within a splice acceptor site. Thus, a splice donor site is the junction between the end of an exon and the start of the intron, typically terminating in the dinucleotide GU. In a preferred embodiment of the present invention, one or both of the terminal GU dinucleotides (or GT dinucleotides in the corresponding DNA sequence) of the splice donor site is/are altered to remove the splice site.

A splice acceptor site is a site in RNA which lies at the 3' side of the RNA which is removed during the splicing process and which contains the site which is cut and rejoined to a nucleotide residue within a splice donor site. Thus, a splice acceptor site is the junction between the end of an intron (typically terminating with the dinucleotide AG) and the start of the downstream exon. In a preferred embodiment of the present invention, one or both of the terminal AG dinucleotides of the splice acceptor site is/are altered to remove the splice site.

Polynucleotides

Polynucleotides used in the invention may comprise DNA or RNA. They may be single-stranded or double-stranded. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides used in the invention to reflect the codon usage of any particular host organism in which the polypeptides are to be expressed. The polynucleotides may be modified by any method available in the art. Such modifications may be carried out in order to enhance the in vivo activity or life span of polynucleotides of the invention.

The polynucleotides used in the invention may encode fusion proteins for example to aid in cellular secretion of the expressed polypeptides. Where, for example, the HSV-tk polypeptide is desired to be expressed from the cell, it may be desirable to add targeting sequences to target the proteins to particular cell compartments or to secretory pathways. Such targeting sequences have been extensively characterised in the art.

Polynucleotides such as DNA polynucleotides may be produced recombinantly, synthetically, or by any means available to those of skill in the art. They may also be cloned by standard techniques.

Longer polynucleotides will generally be produced using recombinant means, for example using PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

It will be appreciated that the polynucleotide of the invention may contain only a coding region for the mutant thymidine kinase. However, it is preferred if the polynucleotide further comprises, in operable linkage, a portion of nucleic acid that allows for efficient translation of the coding sequence in the target cell. It is further preferred if the polynucleotide (when in a DNA form) further comprises a promoter in operable linkage which allows for the transcription of the coding region and the portion of nucleic acid that allows for efficient translation of the coding region in the target cell.

Protein

As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds. The terms subunit and domain may also refer to polypeptides and peptides having biological function.

Variants, Derivatives, Analogues, Homologues and Fragments

In addition to the specific proteins and nucleotides mentioned herein, the present invention also encompasses the use of variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question retains at least one of its endogenous functions. A variant sequence can be obtained by addition, deletion, substitution modification replacement and/or variation of at least one residue present in the naturally-occurring protein.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence retains the required activity or ability. Amino acid substitutions may include the use of non-naturally occurring analogues.

Proteins of use in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the transport or modulation function is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Polynucleotide variants will preferably comprise codon optimised sequences. Codon optimisation is known in the art as a method of enhancing RNA stability and therefor gene expression. The redundancy of the genetic code means that several different codons may encode the same amino-acid. For example, Leucine, Arginine and Serine are each encoded by six different codons. Different organisms show preferences in their use of the different codons. Viruses such as HIV, for instance, use a large number of rare codons. By changing a nucleotide sequence such that rare codons are replaced by the corresponding commonly used mammalian codons, increased expression of the sequences in mammalian target cells can be achieved. Codon usage tables are known in the art for mammalian cells, as well as for a variety of other organisms. Preferably, at least part of the sequence is codon optimised. Even more preferably, the sequence is codon optimised in its entirety.

Vectors

As it is well known in the art, a vector is a tool that allows or facilitates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising the nucleotide sequences used in the invention and/or expressing the proteins used in the invention. Examples of vectors used in recombinant DNA techniques include but are not limited to plasmids, chromosomes, artificial chromosomes or viruses.

Polynucleotides used in the invention are preferably incorporated into a vector. Preferably, a polynucleotide in a vector for use in the invention is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under conditions compatible with the control sequences.

The control sequences may be modified, for example by the addition of further transcriptional regulatory elements to make the level of transcription directed by the control sequences more responsive to transcriptional modulators.

Vectors may be transformed or transfected into a suitable host to provide for expression of the tk gene product. This process may comprise culturing a host cell transformed with an expression vector as described above under conditions to provide for expression by the vector of a coding sequence encoding the protein, and optionally recovering the expressed protein.

The vectors used in the present invention may be for example, plasmid or virus vectors provided with an origin of replication, optionally a promoter for the expression of a polynucleotide and optionally a regulator of the promoter. The vectors may contain one or more selectable marker genes, and/or a traceable marker such as GFP. Vectors may be used, for example, to transfect or transform a host cell.

Control sequences operably linked to sequences encoding proteins for use in the invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Virol promoters may also be used, for example the Moloney murine leukaemia virus long terminal repeat (MMLV LTR) promoter, the rows sarcoma, virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Preferably, the viral vector preferentially transduces a certain cell type or cell types.

Retroviral Vectors

In one embodiment, the vector used in the present invention is a retrovirus based vector which has been genetically engineered so that it can not replicate and produce progeny infectious virus particles once the virus has entered the target cell. There are many retroviruses that are widely used for delivery of genes both in tissue culture conditions and in living organisms. Examples include and are not limited to murine leukemia virus (MLV), human immunodeficiency virus (HIV-1), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses. A detailed list of retroviruses may be found in Coffin et at, 1997, "retroviruses", Cold Spring Harbour Laboratory Press Eds: J M Coffin, S M Hughes, H E Varmus pp 758-763.

The basic structure of a retrovirus genome is a 5' LTR and a 3' LTR, between or within which are located a packaging signal to enable the genome to be packaged, a primer binding site, integration sites to enable integration into a host cell genome and gag, pol and env genes encoding the packaging components—these are polypeptides required for the assembly of viral particles. More complex retroviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration, and transcription. LTRs also serve as enhancer-promoter sequences and can control the expression of the viral genes. Encapsidation of the retroviral RNAs occurs by virtue of a psi sequence located at the 5' end of the viral genome.

The LTRs themselves are identical sequences that can be divided into three elements, which are called U3, R, and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

In a defective retroviral vector genome gag, pol and env may be absent or not functional. The R regions at both ends of the RNA are repeated sequences. U5 and U3 represent unique sequences at the 5' and 3' ends of the RNA genome respectively.

More preferably, the viral vector is a targeted vector, that is it has a tissue tropism which is altered compared to the native virus, so that the vector is targeted to particular cells. This may be achieved by modifying the retroviral Env protein. Preferably the envelope protein is a non-toxic envelope or an envelope which may be produced in non-toxic amounts within the primary target cell, such as for example a MMLV amphotropic envelope or a modified amphotropic envelope.

Preferably the envelope is one which allows transduction of human cells. Examples of suitable env genes include, but are not limited to, VSV-G, a MLV amphotropic env such as the 4070A env, the RD114 feline leukaemia virus env or haemagglutinin (HA) from an influenza virus. The Env protein may be one which is capable of binding to a receptor on a limited number of human cell types and may be an engineered envelope containing targeting moieties. The env and gag poi coding sequences are transcribed from a promoter and optionally an enhancer active in the chosen packaging cell line and the transcription unit is terminated by a polyadenylation signal. For example, if the packaging cell is a human cell, a suitable promoter-enhancer combination is that from the human cytomegalovirus major immediate early (hCMV-MIE) gene and a polyadenylation signal from SV40 virus may be used. Other suitable promoters and polyadenylation signals are known in the art.

MLV

Preferably, the retroviral vector used in the present invention is an Murine Leukemia Virus (MLV) vector. Retroviral vectors derived from the amphotropic Moloney murine leukemia virus (MLV-A) are commonly used in clinical protocols worldwide. These viruses use cell surface phosphate transporter receptors for entry and then permanently integrate into proliferating cell chromosomes. The genes are then maintained for the lifetime of the cell. Gene activity on MLV based constructs are easy to control and can be effective over a long time. Clinical trials conducted with these MLV-based systems have shown them to be well tolerated with no adverse side effects.

An example of an MLV vector for use in the present invention is a vector derived from SFCMM-3, which carries both the suicide gene HSV-tk and the marker gene ΔLNGFR (Verzeletti 98, Human Gene Therapy 9:2243). The original vector used in the preparation of SFCMM-3 is LXSN (Miller et al. Improved retroviral vectors for gene transfer and expression. BioTechniques 7:980-990, 1989) (Genebank accession #28248). LXSN vector was modified by the insertion of the HSV-tk gone into the unique Hpa I site ("blunt cut"), removal of the neo gene by digestion with Hind III and Nae I, and insertion of the cDNA encoding ΔLNGFR in this site.

Lentiviral Vector

In one embodiment, the vector of the present invention may be a lentiviral vector. Lentivirus vectors are part of a larger group of retroviral vectors. A detailed list of lentiviruses may be found in Coffin et al ("Retroviruses" 1997 Cold Spring Harbour Laboratory Press Eds: J M Coffin, S M Hughes, H E Varmus pp 758-763). In brief, lentiviruses can be divided into primate and non-primate groups. Examples of primate lentiviruses include but are not limited to: the human immunodeficiency virus (HIV), the causative agent of human acquired-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis, 1992; Lewis and Emerman, 1994). In contrast, other retroviruses—such as MLV—are unable to infect non-dividing or slowly dividing cells such as those that make up, for example, muscle, brain, lung and liver tissue. As lentiviruses are able to transduce terminally differentiated/primary cells, the use of a lentiviral screening strategy allows library selection in a primary target non-dividing or slowly dividing host cell.

Adenovirus Vectors

In another embodiment, the vector of the present invention may be an adenovirus vector. The adenovirus is a double-stranded, linear DNA virus that does not go through an RNA intermediate. There are over 50 different human serotypes of adenovirus divided into 6 subgroups based on the genetic sequence homology. The natural target of adenovirus is the respiratory and gastrointestinal epithelia, generally giving rise to only mild symptoms. Serotypes 2 and 5 (with 95% sequence homology) are most commonly used in adenoviral vector systems and are normally associated with upper respiratory tact infections in the young.

Adenoviruses are nonenveloped, regular icosohedrons. A typical adenovirus comprises a 140 nm encapsidated DNA virus. The icosahedral symmetry of the virus is composed of 152 capsomeres: 240 hexons and 12 pentons. The core of the particle contains the 36 kb linear duplex DNA which is covalently associated at the 5' ends with the Terminal Protein (TP) which acts as a primer for DNA replication. The DNA has inverted terminal repeats (ITR) and the length of these varies with the serotype.

The adenovirus is a double stranded DNA nonenveloped virus that is capable of in vivo and in vitro transduction of a broad range of cell types of human and non-human origin. These cells include respiratory airway epithelial cells, hepatocytes, muscle cells, cardiac myocytes, synoviocytes, primary mammary epithelial cells and post-mitotically terminally differentiated cells such as neurons.

Adenoviral vectors are also capable of transducing non dividing cells. This is very important for diseases, such as cystic fibrosis, in which the affected cells in the lung epithelium, have a slow turnover rate. In fact, several trials are underway utilising adenovirus-mediated transfer of cystic fibrosis transporter (CFTR) into the lungs of afflicted adult cystic fibrosis patients.

Adenoviruses have been used as vectors for gene therapy and for expression of heterologous genes. The large (36 kilobase) genome can accommodate up to 8 kb of foreign insert DNA and is able to replicate efficiently in complementing cell lines to produce very high titres of up to $10^{12}$. Adenovirus is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome.

Instead, it functions episomally (independently from the host genome) as a linear genome in the host nucleus. Hence the use of recombinant adenovirus alleviates the problems associated with random integration into the host genome.
Pox Virol Vectors Pox viral vectors may be used in accordance with the present invention, as large fragments of DNA are easily cloned into their genome and recombinant attenuated vaccinia, variants have been described (Meyer, et al., 1991; Smith and Moss, 1983).

Examples of pox viral vectors include but are not limited to leporipoxvirus: Upton, et at, 1986, (shope fibroma virus); capripoxvirus: Gershon, et al., 1989, (Kenya sheep-1); orthopoxvirus: Weir, et at, 1983, (vaccinia); Esposito, et al., 1984, (monkeypox and variola virus); Hruby, et at, 1983, (vaccinia); Kilpatrick, et al., 1985, (Yaba monkey tumour virus); avipoxvirus: Binns, et al., (1988) (fowlpox); Boyle, et al., 1987, (fowlpox); Schnitzlein, et at, 1988, (fowlpox, quailpox); entornopox (Lytvyn, et al., 1992.

Poxvirus vectors are used extensively as expression vehicles for genes of interest in eukaryotic cells. Their ease of cloning and propagation in a variety of host cells has led, in particular, to the widespread use of poxvirus vectors for expression of foreign protein and as delivery vehicles for vaccine antigens (Moss, 1991).
Vaccinia Virol Vectors The vector of the present invention may be a vaccinia virus vector such as MVA or NYVAC. Most preferred is the vaccinia strain modified virus ankara (MVA) or a strain derived therefrom. Alternatives to vaccinia vectors include avipox vectors such as fowlpox or canarypox known as ALVAC and strains derived therefrom which can infect and express recombinant proteins in human cells but are unable to replicate.
Delivery Systems The invention further provides a delivery system for mutant tk polynucleotide of the present invention.

The delivery system of the present invention may be a viral or non-viral delivery system. Non-viral delivery mechanisms include but are not limited to lipid mediated transfection, liposomes, immunoliposomes, lipofectin, cationic, facial amphiphiles (CFAs) and combinations thereof.

The polynucleotides may be delivered to the target cell population by any suitable Gene Delivery Vehicle, GDV. This includes but is not restricted to, DNA, formulated in lipid or protein complexes or administered as naked DNA via injection or biolistic delivery, viruses such as retroviruses, adenoviruses, poxvirus, lentiviruses, herpes viruses, vaccinia viruses, adeno associated viruses, murine leukemia viruses, semliki forest viruses and baculoviral viruses. Alternatively, the polynucleotides are delivered by cells such as monocytes, macrophages, lymphocytes or hematopoietic stem cells. In particular a cell-dependent delivery system is used. In this system the polynucleotide encoding the TK protein are introduced into one or more cells ex viva and then introduced into the patient.

The agents of the present invention may be administered alone but will generally be administered as a pharmaceutical composition.
Host Cells Vectors and polynucleotides of the invention may be introduced into host cells for the purpose of replicating the vectors/polynucleotides and/or expressing the TK encoded by the polynucleotide of the invention. The host cell may be a bacterial cell or a eukaryotic cell, for example a yeast, insect or a mammalian cell.

The host cell may be a cell for packaging and propagating a virus, such as retroviral packaging cell lines which are well known in the art.

The host cell may be a cell in an animal or patient (whether human or animal) which it is desired to destroy. The polynucleotide and vector of the present invention are useful to target to cells to be destroyed. Cells expressing TK may be contacted with an agent which is substantially non-toxic which is converted to a toxic form by TK.
Method of Destroying Cells In one aspect of the present invention there is provided a method of destroying cells comprising
  (i) introducing into said cells a polynucleotide or a vector of the present invention;
  (ii) allowing said cells to express thymidine kinase; and contacting said cells with a substantially non-toxic agent which is converted by thymidine kinase to a toxic agent.

The introduction into the cells of the polynucleotide or vector, and the contacting of the cells with the substantially non-toxic agent, may be in any order. The cells to be destroyed may be in vitro, such as cells which are grown in culture, or they may be cells which are part of an animal. Representative examples of cells which it is desired to destroy are T-cells, autoimmune cells, tumor cells, cells which do not express or inappropriately express a particular gene, and cells infected with bacteria, viruses, or other intracellular parasites.
Treatment It is to be appreciated that all references herein to treatment include curative, palliative and prophylactic treatment.

The treatment of mammals is particularly preferred. Both human and veterinary treatments are within the scope of the present invention.

In one aspect of the present invention there is provided a method of treating a patient with cells in need of destruction comprising
(i) introducing into the patient a polynucleotide, a vector or a pharmaceutical composition of the present invention;
(ii) allowing said polynucleotide or expression vector to be taken up by said cells;
(iii) allowing said cells to express thymidine kinase; and
(iv) introducing into the patient a substantially non-toxic agent which is converted by thymidine kinase to a toxic agent.

In another aspect of the present invention there is provided a method of treating a patient with cells in need of destruction comprising
(i) removing the cells from the patient or donor cells;
(ii) introducing into the cells ex vivo a polynucleotide or an expression vector of the present invention;
(iii) introducing the modified cells into the patient;
(iv) allowing the cells to express thymidine kinase; and administering to the patient a substantially non-toxic agent which is converted by thymidine kinase into a toxic agent.

Representative examples of diseases which can be treated by polynucleotides, vectors and methods of the present invention include diseases such as cancer, hyperkeratosis, prostate hypertrophy, hyperthyroidism, a wide variety of endocrinopathies, autoimmune diseases, allergies, restenosis, a wide variety of viral diseases such as HIV and AIDS, hepatitis and intracellular parasitic diseases.

The polynucleotides, vectors and methods of the present invention may be used in the course of therapy following allogeneic bone marrow transplant. Allogeneic bone marrow transplant is the treatment of choice for many hematologic malignancies, such as leukemia, lymphoma and multiple myeloma. Transplantation of allogeneic bone marrow, particularly when employed with high dose chemoradiotherapy, has been shown to produce superior results compared to autologous or syngeneic transplants.

In performing allogeneic bone marrow transplant alloreactive T lymphocytes may be removed from the graft to prevent graft versus host disease (GvHD). GvHD occurs when T-cells in the transplanted stem cell graft may begin to attack the recipient's body. However, such removal of cells can increases the incidence of disease relapse, graft rejection and reactivation of viral infection. To counter these effects, allogeneic bone marrow transplant patients can be treated by introducing donor T lymphocytes after a delay following the allogeneic bone marrow transplant. The therapeutic promise of delayed introduction of donor T lymphocytes following allogeneic bone marrow transplant, however, is limited by GvHD, a frequent and potentially lethal complication of the treatment. This problem has been addressed by the administering to a patient T-cells genetically engineered to include a polynucleotide encoding a "suicide gene". The polynucleotides and vectors of the present invention encoding the mutant TK may be been used in this regard.

Thus, in one aspect of the present invention there is provided a method of preventing graft-versus-host disease in a patient comprising
(i) administering to a host T-cells genetically engineered to include a polynucleotide or vector of the present invention; and
(ii) administering to said host, prior to the occurrence of graft-versus-host disease, a substantially non-toxic agent in an amount effective to kill genetically engineered T-cells capable of providing a graft-versus-host effect in said patient through interaction of said agent with thymidine kinase.

The cells comprising the polynucleotide or vector encoding the mutant tk gene preferably comprises a marker gene which may be used to monitor the presence of the mutant tk gene. Preferably, the marker gene is encoded by the polynucleotide or expression vector of the present invention. An example of one such marker gene is a modified low affinity nerve growth factor receptor ($\Delta$LNGFR). Modified LNGFR, when expressed on the surface of transduced cells retains the binding properties of the corresponding unmodified NGF receptor with respect to its ligand, yet cannot effect signal transduction as a result of ligand binding. Examples of specific LNGFR modifications are described in U.S. application Ser. No. 08/602,791.

Pharmaceutical Compositions

A pharmaceutical composition is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Further preferred features and embodiments of the present invention will now be described by way of non-limiting example and with reference to the accompanying drawings.

BRIEF DESCRIPTION OF THE DRAWINGS

FIGS. 1A, 1B, and 1C, show the multiple alignment of nucleotide sequences of HSV-1 thymidine kinase gene (HSV-tk) mutants (TkMut2 (SEQ ID NO 2), TkMut23 (SEQ ID NO:3), TkMut24 (SEQ ID NO:4), TkMut34 (SEQ ID NO:5), TkMut4 (SEQ ID NO:6) and TkMut234 (SEQ ID NO: 7). Bases are numbered from the ATG start codon of wild-type HSV-tk sequence. Sequences are aligned against the TK wt sequence (TK wt, SEQ ID NO:1). The position of mutations is indicated by a number above the alignment. Mutations at positions (330), (541 and 542), and (555) are represented by the numbers 2, 3 and 4 respectively.

FIG. 2 shows the splicing consensus sequence.

FIG. 5 shows the sequence of the critical portion of the HSV-tk gene in SFCMM-3 (SEQ ID NO: 8) versus TK3 (scSFCMM-3) (SEQ ID NO: 9). The nucleotide positions different between SFCMM-3 and TK3 (scSFCMM-3) vectors are bordered by a square. The gene segments which are deleted in the spliced forms of SFCMM-3 and TK3 are indicated in italics. The corresponding splicing donor and acceptor sites are indicated.

FIG. 6 shows a schematic summary of the mutations introduced into the SFCMM-3 vector. The depicted nucleotide sequence of the donor site is set forth in SEQ ID NO: 10. The depicted DNA sequence of the acceptor site is set forth in SEQ ID NO: 12. The depicted amino acid sequence of the donor site is set forth in SEQ ID NO: 11. The depicted amino acid sequence of the acceptor site is set forth in SEQ ID NO: 13.

Figure 3:
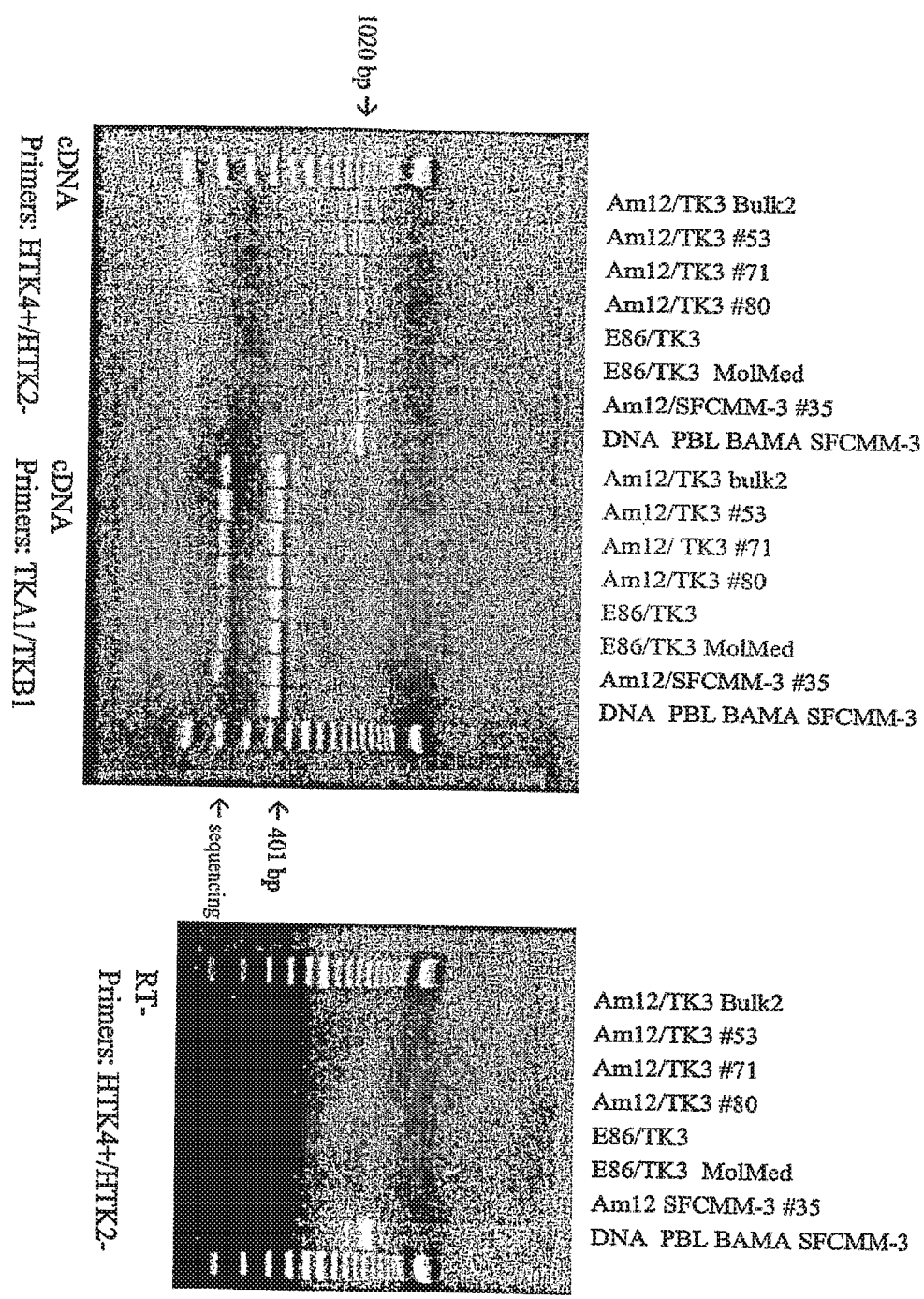
FIG. 3 shows the HSV-tk PCR product of cDNA prepared from the supernatant of echotropic packaging cell line GP+E86 and from the amphotropic packaging cell line gp+env Am12 (Am12) transfected with SFCMM-3 (Verzeletti, 1998, *Human Gene Therapy* 9:2243-2251) and/or TK3 (scSFCMM-3) (Chalmers, 2001) vector.

EXAMPLE 1—RELATIVE FREQUENCY OF THE SPLICED FORM OF HSV-TK IN SFCMM-3#35 SUPERNATANT AND TRANSDUCED CELLS

The relative frequency of the spliced form (percent spliced form versus spliced plus unspliced) was evaluated by two quantitative real-time RT-PCR (RNA from supernatant) or PCR (DNA from transduced lymphocytes), specific for each HSV-tk form, using TaqMan 7700 system.

Materials and Methods

SFCMM-3 Retroviral Vector

The GP+envAm12 (Am12)-derived producer cell line, SFCMM-3 clone 35 (Am12/SFCMM-3#35), was expanded 5 days in DMEM (Cambrex) medium containing 2 mM glutamine and 10% of irradiated FBS (Hyclone). Retroviral supernatants were harvested from confluent flasks in X-VIVO 15 medium (Cambrex) supplemented with 2 mM glutamine after 24 h incubation of the cells at 33° C. Virus-containing supernatants were filtered and stored at −80° C. until further use.

T Cell Transduction

Peripheral blood mononuclear cells were collected from healthy donors and isolated by centrifugation on Lymphoprep (Nycomed).

Peripheral blood lymphocytes (PBLs) were stimulated with OKT3 (30 ng/ml) (Orthoclone) and cultured in RPMI (Hyclone) containing 3% of autologus plasma, 2 mM glutamine and supplemented with recombinant human interleukin 2, 600 IU/ml (Proleukin). Transduction of PBLs was performed by centrifugation of retroviral vector particles (supernatant from Am12/SFCMM-3#35) on OKT3-stimulated PBLs.

Two centrifugation cycles were performed on the second and the third day after OKT3 stimulation.

After the transduction phase, lymphocytes were collected and the percentage of actually transduced cells evaluated by FACS analysis, thanks to the ΔLNGFR molecule, used as a cell surface marker. The transduced cells were then sorted by antibodies conjugated to magnetic beads (Dynabeads), expanded a few days in culture, and then frozen after a total of 10 days in culture.

Samples Preparation

DNA was purified from 1-2×10$^6$ cells by using QIAamp DNA Mini kit (Qiagen) following manufacturer's protocols and yield was determined by measuring the OD$_{260}$. RNA was purified from 140 µl of supernatant by using QIAamp Virol RNA Mini. Kit (Qiagen) according to the manufacturer's protocols. 13.5 µl of purified RNA were first subjected to DNase treatment at 25° C. for 20 min, and 95° C. for 5 min to inactivate DNase. Half of the DNase-treated RNA was then reverse transcribed at 42° C. for 1 h using M-MLV Reverse Transcriptase (Invitrogen) and Oligo dT. Synthesized cDNA was 5-fold diluted before using in the Real time PCR.

Quantitation of Spliced Form by Real Time PCR

DNA standard curve has been prepared by subcloning the unspliced and truncated form of HSV-tk into pCR2.1 TOPO vector (Invitrogen). Two different sets of primers and probes have been designed using Primer Express™ 1.5 software (PE Applied Biosystems), able to selectively amplify and detect the unspliced and the spliced form of HSV-tk. Two quantitative real time PCRs were set-up, specific for each HSV-tk form, using TaqMan/ABI PRISM 7700 sequence detection system.

To set up a Quantitative Real time PCR specific for the HSV-tk unspliced form, primers and probe were designed in the spliced region of HSV-tk gene. Real Time PCR for the unspliced form was performed in a 25 µl reaction mixture containing 100-500 ng of genomic DNA or 10 µl of cDNA prepared as described above, 1× TaqMan Universal PCR Master Mix (PE Applied Biosystems) 300 nM of each of the two primers TKwt for (5'-CGG CGG TGG TAA TGA CAA G-3'; SEQ ID NO: 14) and Tkwtrev (5'-GCG TCG GTC ACG GCA TA-3'; SEQ ID NO: 15) and 200 nM of TKwt MOB probe (5'-FAM CCA GAT AAC AAT GGG C-3'; SEQ ID NO: 16).

A TaqMan probe encompassing the splice junction was designed to selectively detect the HSV-tk spliced form. Quantitative Real time PCR specific for the TK spliced (truncated) form was performed in a 25 µl reaction mixture containing 100-500 ng of genomic DNA or 10 µl of cDNA prepared as described above, 1× Master Mix (PE Applied Biosystems) 300 nM of each of the two primers TKSP18 (5'-GGA TGA GGG CCA CGA A-3'; SEQ ID NO: 17) and TKSP16 (5'-CGA ACA TCT ACA CCA CAC AAC A-3'; SEQ ID NO: 18) and 200 nM of Taq Man probe PSP10 (5' FAM-CCA GCA GCA COG CCC TOG TCG-TAMRA 3'; SEQ ID NO: 19). Thermal cycling conditions were as follows: initial activation of UNG at 50° C. for 2 min, followed by activation of Taq Gold and inactivation of UNG at 95° C. for 15 min. Subsequently, 40 cycles of amplification were performed at 95° C. for 15 s and 60° C. for 1 min. Both PCRs were performed in parallel in MicroAmp optical 96-well reaction plates (Applied Biosystems) using the ABI Prism 7700 Sequence Detection Systems (Applied Biosystems). Mean baseline fluorescence was calculated from PCR cycles 3 to 15, and Ct was defined as the PCR cycle in which the normalized fluorescence intensity of the reporter dye equaled 0.05. Two standard curves with known copy numbers (from $10^6$ to 4 copies/reaction) were generated in each TaqMan assay by plotting the Ct values against the logarithm of the initial input of DNA amount. Standard dilutions and cDNA samples were analyzed in duplicate and triplicate, respectively. Both PCRs were validated and showed extended dynamic range (6 log), high sensitivity (<10 copies/reaction) good reproducibility (CV<5%) and repeatability (CV<5%).

Results

The results are shown in Table 1. Six clinical grade lots of SFCMM-3 vector supernatant were analysed, as well as nine preparations of transduced lymphocytes.

The relative frequency of the spliced form is below 5% in all 6 clinical grade lots of SFCMM-3 supernatant (1.12+/−0.75, range 0.65-2.60), as well as in 9 preparations of T lymphocytes transduced with SFCMM-3 supernatant (1.89+/−1.22, range 0.84-4.00).

EXAMPLE 2—VARIANT OF SPLICED TK INS SCSFCMM-3 SUPERNATANTS AND TRANSDUCED CELLS

Materials and Methods scSFCMM-3 Retroviral Vector and Producer Cell Lines

Vector DNA TK3 (TK3 Molmed and TK3 are different preparations of the same plasmid scSFCMM-3, described in: Chalmers 2001, *Molecular Therapy* 4:146-148) was transfected into the echotropic packaging cell line GP+ E-86 (E86) by calcium phosphate coprecipitation. The supernatant obtained from the transient transfection of E86 cells was filtered and then used to infect the Am12 cell line. The fraction of cells containing TK3 was isolated by using immunomagnetic selection and the resulting Am12/TK3 bulk culture was expanded. After limiting dilution of the Am12/TK3 bulk culture, clones #53, #71, and #80 were selected on the basis of high growth capacity and transduction efficiency on T lymphocytes.

The Am12/TK3 clones were expanded in DMEM (Cambrex) containing 2 mM glutamine and 10% irradiated FBS (Hyclone). Retroviral supernatants were harvested in X-VIVO 15 medium (Cambrex) supplemented with 2 mM glutamine after 24 h incubation of the cells at 33° C. Virus-containing supernatants were filtered with 0.22 µm filters and stored at −80° C. until further use.

T Cell Transduction

Peripheral blood mononuclear cells were collected from several healthy donors and isolated by centrifugation on Lymphoprep (Nycomed).

Peripheral blood lymphocytes (PBLs) were stimulated with OKT3 (30 ng/ml) (Orthoclone) and cultured in RPMI (Hyclone) containing 3% of autologus plasma, 2 mM glutamine and supplemented with recombinant human interleukin 2, 600 IU/ml (Proleukin). Transduction of PBLs was performed by centrifugation of retroviral vector particles on OKT3-stimulated PBLs. Two centrifugation cycles were performed on the second and the third day after OKT3 stimulation.

After the transduction phase, PBLs were collected and the percentage of actually transduced cells evaluated by FACS analysis, thanks to the ΔLNGFR molecule, used as a cell surface marker. The transduced cells were then sorted by antibodies conjugated to magnetic beads (Dynabeads), expanded a few days in culture, and pellets were prepared for PCR analysis.

Polymerase Chain Reaction

The bulk producer cell line (Am12/TK3 Bulk 2) as well as single producer cell clones obtained by limiting dilution (Am12/TK3 #53, #71 and #80) were analysed. RNA was extracted from the culture supernatants containing infectious viral particles.

RT-PCR was performed with HTK4+ (5'-TTC TCT AGG CGC CCG AAT TCG TT-3'; SEQ ID NO: 20) and HTK2- (5'-ATC CAG GAT AAA GAC GTG CAT GG-3'; SEQ ID NO: 21) primers or TKA1 (5'-COT ACC CGA GCC GAT GAC TT-3'; SEQ ID NO: 22) and TKB1 (5'-TGT GTC TOT CCT CCG GAA GG-3'; SEQ ID NO: 23) primers. RT PCR was performed using Titan One tube RT-PCR System (Roche) in a 50 µl reaction mixture containing 10 µl of RNA DNase-treated, 1×RT-PCR Buffer with 1.5 mM of $MgCl_2$ (PE Applied Biosystems), 200 µM of each deoxynucleotide (dNTP), 200 nM of each primer, 5 mM of dithiothreitol (DTT), 20 U of RNase Inhibitor, 1 µl of Titan Enzyme mix.

Supernatants from Am12/SFCMM-3 #35 and DNA from SFCMM-3 transduced lymphocytes were used as controls. RT-controls were also run in parallel.

The RT-PCR cycling profile consisted of a first reverse transcription step for 30 min at 50° C., a denaturation step for 2 min at 94° C. followed by 40 cycles with denaturation for 30 s at 95° C., annealing for 30 s at 60° C. and elongation for 1 min 30 s at 68° C., and one final elongation step of 10 min at 68° C. Ten microliters of amplified product were analyzed by agarose gel electrophoresis.

Genomic DNA was extracted from PBLs of several donors transduced with SFCMM-3 or TK3 vector. PCR was performed in a 25 µl reaction mixture containing 100-500 ng of genomic DNA, 1×PCR Buffer with 1.5 mM of MgCl$_2$ (Applied Biosystems), 200 µM of each dNTP, 1600 nM of each primer TK2S (5'-CCA TAG CAA CCG ACG TAC G-3'; SEQ ID NO: 24) and TKAS (5'-GAA TCG CGG CCA GCA TAG C-3'; SEQ ID NO: 25), The PCR cycling profile consisted of a first denaturation step 15 min at 94° C. followed by 38 cycles with denaturation for 1 min of 95° C., annealing for 30 s at 65° C. and extension for 1 min at 72° C., and one final extension step of 10 min at 72° C. Ten microliters of amplified product were analyzed by agarose gel electrophoresis.

On the same samples PCR was performed in a 25 µl reaction mixture containing 100-500 ng of genomic DNA, 1×PCR Buffer with 1.5 mM of MgCl$_2$ (Applied Biosystems), 200 µM of each dNTP, 300 nM of each primer HTK4+ (5'-TTC TCT AGG CGC CGG AAT TCG TT-3'; SEQ ID NO: 20) and HTK2-(5'-ATC CAG GAT AAA GAC GTG CAT GG-3'; SEQ ID NO: 21), 1.25 U of AmpliTaq Gold (Applied Biosystems). The PCR cycling profile consisted of a first denaturation step 15 min at 94° C. followed by 40 cycles with denaturation for 30 s at 95° C., annealing for 50 s at 600 C and extension for 1 min at 72° C., and one final extension step of 10 min at 72° C. Ten microliters of amplified product were analyzed by agarose gel electrophoresis.

cDNA Sequence Analysis of the TK3 Spliced Form

The lower band of the product amplified with HTK4+/HTK2-primers from Am12/TK3#53 supernatant was sequenced by using an automated fluorescent DNA sequence apparatus. Sequence was carried out by PRIMM (Milan, Italy).

Results

HSV-tk RT-PCR from RNA of Culture Supernatants

Two PCR products were detected analyzing RNA from SFCMM-3 as well as TK3 vectors, produced by Am12 and E86 packaging cell lines (FIG. 3). The TK3 vector corresponds to the described scSFCMM-3 vector (Chalmers, 2001). The major product (upper band) corresponds to the unspliced form of HSV-tk (1020 base pair (bp) with HTK4+/HTK2-primers; 401 bp with TKA1/TKB1 primers) in all the samples. The size of the minor product (lower band) in the SFCMM-3 samples corresponds to the described spliced form, in which 227 bp are deleted (Garin 2001, *Blood* 97:122-129).

On the contrary, the size of the minor product in the TK3 samples is slightly larger, suggesting the presence of a different spliced form, in which a smaller fragment is deleted; this difference between SFCMM-3 and TK3 samples is particularly evident with TK2S/TKAS primers. Additional, intermediate products observed with HTK4+/HTK2-primers only are considered as possible PCR artifacts.

HSV-tk PCR on DNA from Transduced Lymphocytes

Figure 4:
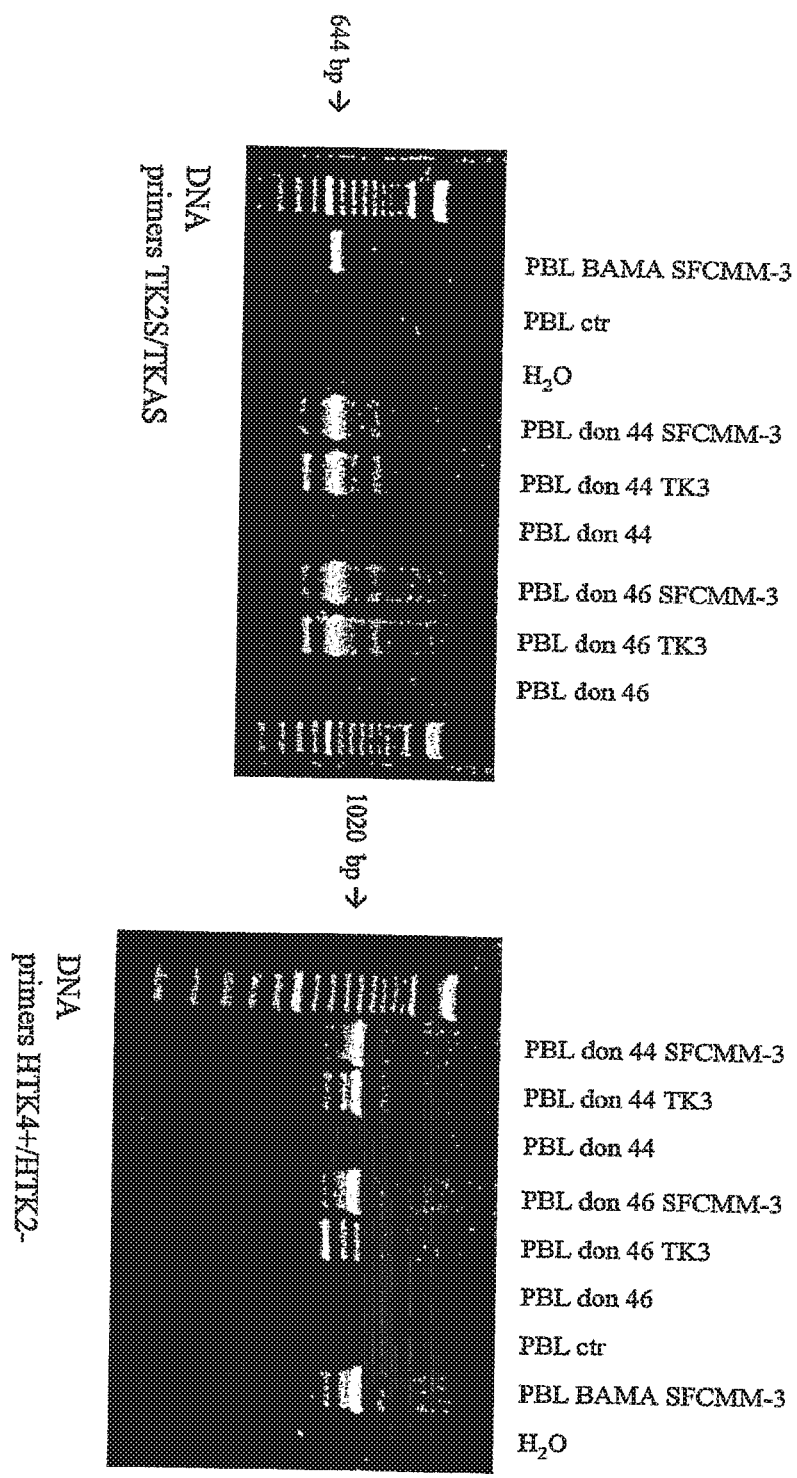
FIG. 4 shows PCR amplified HSV-tk in peripheral blood lymphocytes (PBL) transduced with SFCMM-3 and/or TK3 (scSFCMM-3) vector.

Two PCR products were detected analyzing DNA from SFCMM-3 as well as TK3 transduced PBLs (FIG. 4). The major product (upper band) corresponds to the unspliced form of HSV-tk (644 bp with TK2S/TKAS primers; 1020 hp with HTK4+/HTK2-primers). The size of the lower band (corresponding to the described spliced form) in the SFCMM-3 samples is 417 bp with TK2S/TKAS printers and 793 bp with HTK4+/HTK2-primers.

Sequence of the Critical Portion of the HSV-tk Gene in SFCMM-3 Versus TK3.

The sequence of the critical portion of the HSV-tk gene in SFCMM-3 versus TK3 is shown in FIG. 5. The gene segments which are deleted in the spliced forms of SFCMM-3 and TK3 are indicated in italics. The corresponding splicing donor and acceptor sites are underlined.

The sequence data confirm that different spliced forms are generated in SFCMM-3 (227 bp deletion) and in TK3 (214 bp deletion) samples. As expected in both cases the GU and AG dinucleotides are present at 5' and 3' borders of the deleted sequence, respectively.

EXAMPLE 3—ELIMINATION OF SPLICING BY SITE DIRECT MUTAGENESIS

Materials and Methods

Starting from the wild type SFCMM-3 vector, recombinant plasmids were prepared by site-directed mutagenesis with different mutations in the HSV-tk gene (FIG. 6). Third-base degenerate changes were introduced thus in all instances the wild type amino acid sequence of HSV-tk enzyme was preserved.

Site-Directed Mutagenesis

To generate pcDNA3.1-tk plasmid, SFCMM-3 plasmid was digested with EcoRI and XhoI and the EcoRI/XhoI fragment was ligated to EcoRI/XhoI digested poDNA3.1 (Invitrogen).

From the pcDNA3.1-tk plasmid, all the HSV-tk mutants were generated by site-directed mutagenesis using the QuickChange Site-Directed Mutagenesis kit (Stratagene). The oligonucleotide primers used to introduce the desired mutation were each complementary to opposite strands of the vector. The sequences of sense primers are reported in the following table:

| Position of mutation | SEQ ID NO: | Oligo sequence[a] | Mutant generated | Plasmid clone[b] |
|---|---|---|---|---|
| t330c | 30 | 5'-CCTCGACCAGGGCGAGATATCGGCCG-3' | TkMut2 | 10.1 |
| t330c | 31 | 5'-CCTCGACCAGGGCGAGATATCGGCCG-3' | TkMut24 | 177.3 |
| g555a | 32 | 5'-ATGACCCCCCAAGCCGTGCT GGCG-3' | TkMut24 | 177.3 |
| a541t/g542c/g555a | 33 | 5'-TACCTTATGGGCTCCATGACCCCCCAAGCCGTGC-3' | TkMut34 | 57.1 |
| g555a | 34 | 5'-ATGACCCCCCAAGCCGTGCTGGCG-3' | TkMut4 | 19.1 |
| t330c | 35 | 5'-CCTCGACCAGGGCGAGATATCGGCCG-3' | TkMut223 | 171.1 |
| a541t/g542c/g555a | 36 | 5'-TACCTTATGGGCTCCATGACCCCCCAAGCCGTGC-3' | TkMut223 | 171.1 |

[a]The position of nucleotide mutations are underlined in bold.
[b]The numbers refer to the number of each SFCMM-3 HSV-tk plasmid clone mutant.

The resulting vectors were sequenced to confirm the corrected nucleotide substitutions. HSV-tk mutated fragment was then removed from pcDNA3.1 by digestion with EcoRI and XhoI, then cloned into SFCMM-3 plasmid to generate SFCMM-3 HSV-tk mutants.

After sequence confirmation of SFCMM-3 HSV-tk mutants (FIGS. 1A-1C), one plasmid clone of each type was used to transiently transfect E86 cells. SFCMM-3 and TK3 plasmids were used as controls. The supernatant was collected from the E86 cultures and used to stably transduce the amphotropic packaging cell line Am12 as described in Materials and Methods section of Example 2. The resulting cell populations were selected for ΔLNGFR expression.

RNA was extracted from the E86 as well as Am12 culture supernatants containing infectious retroviral particles. RT-PCR reactions were carried out on RNA from E86 and Am12 supernatants using TKA1 and TKB1 primers according to the protocol described in Materials and Methods section of Example 2.

Transduction and PCR Analysis of GEM A301 Cell Line and PBLs

CEM A301 cells were cultured in RPMI 1640 (Hyclone) supplemented with 10% FBS (Hyclone) and 2 mM glutamine. CEM A301 cells were infected with Am12 culture supernatant containing SFCMM-3 HSV-tk mutants 2 and 234. The day before transduction $5\times10^5$ cells/ml were cultured. Transduction was then performed by one centrifugation cycle of retroviral vector particles on cells. After the transduction phase, cells were collected and the percentage of actually transduced cells evaluated by FACS analysis. PBLs from three different donors were transduced (as described in Materials and Methods section of Example 2) with Am12 supernatant containing SFCMM-3 HSV-tk mutant 2 as well as SFCMM-3.

The transduced cells were then sorted for ΔLNGFR expression and expanded a few days in culture.

One pellet for PCR analysis was prepared from the transduced non selected cells as well as from transduced selected cells as described in Materials and Methods section of Example 2. Genomic DNA was extracted from pellet cells and PCR reaction was carried out with TKA1 and TKB1 or TKY1 and TKY2 or TKZ1 and TKZ2 primers (as indicated in the table below) in a 25 μl reaction mixture containing 100-500 ng of genomic DNA, 1×PCR Buffer with 1.5 mM of $MgCl_2$ (Applied Biosystems), 200 nM of each dNTPs, 300 nM of each primer, 1.25 Units of AmpliTaq Gold (Applied Biosystems). The PCR cycling profile consisted of a first denaturation step for 15 min at 94° C. followed by 40 cycles with denaturation for 30 s at 94° C., annealing for 50 s at 60° C. and extension for 1 min at 72° C., and one final extension step of 10 min at 72° C., and one final extension step of 10 min at 72° C. Ten microliters of amplified product were analyzed by agarose gel electrophoresis.

| Primer name | Primer sequence | SEQ ID NO: | PCR product length (HSV-tk unspliced) |
| --- | --- | --- | --- |
| TKA1 | 5'-CGT ACC CGA GCC GAT GAC TT-3' | 22 | 401 bp |
| TKB1 | 5'-TGT GTC TGT CCT CCG GAA GG-3' | 23 | |
| TKY1 | 5'-TTA TAT AGA CGG TCC TCA CGG G-3' | 26 | 542 bp |
| TKY2 | 5'-CCA GCA TAG CCA GGT CAA GC-3' | 27 | |
| TKZ1 | 5'-GCC ACC ATG GCT TCG TAC-3' | 28 | 1149 bp |
| TKZ2 | 5'-CGA GTT AAT TCT CAG TTA GCC TCC-3' | 29 | |

Results

Splicing Properties of HSV-tk Mutants in E86 Supernatants

Figure 7:
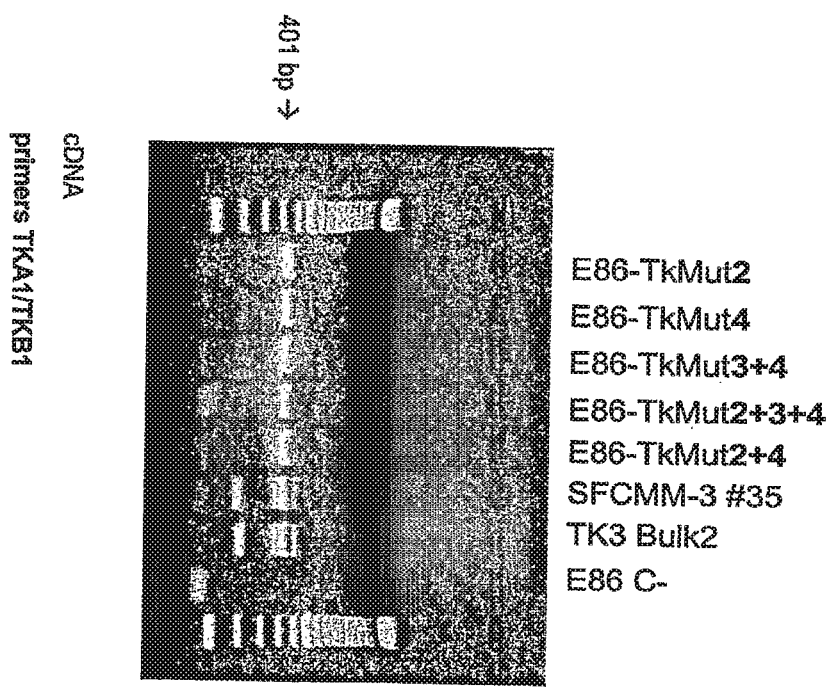
FIG. 7 shows HSV-tk PCR product of cDNA derived from supernatants of E86 cells transiently transfected with recombinant plasmids derived from SFCMM-3 comprising the HSV-tk mutants shown in FIGS. 1A-1C.

The major product (upper band) corresponding to the unspliced form of HSV-tk (401 bp) is detected in all the samples except the negative control (supernatant from non transfected E86 cells, E86 C-) (FIG. 7).

The minor product (lower band) is less abundant in RNA from all the mutant vectors, in respect to SFCMM-3 and TK3 vectors, produced by E86 packaging cell lines.

Splicing Properties of HSV-tk Mutants in Am12 Supernatants

Figure 8:
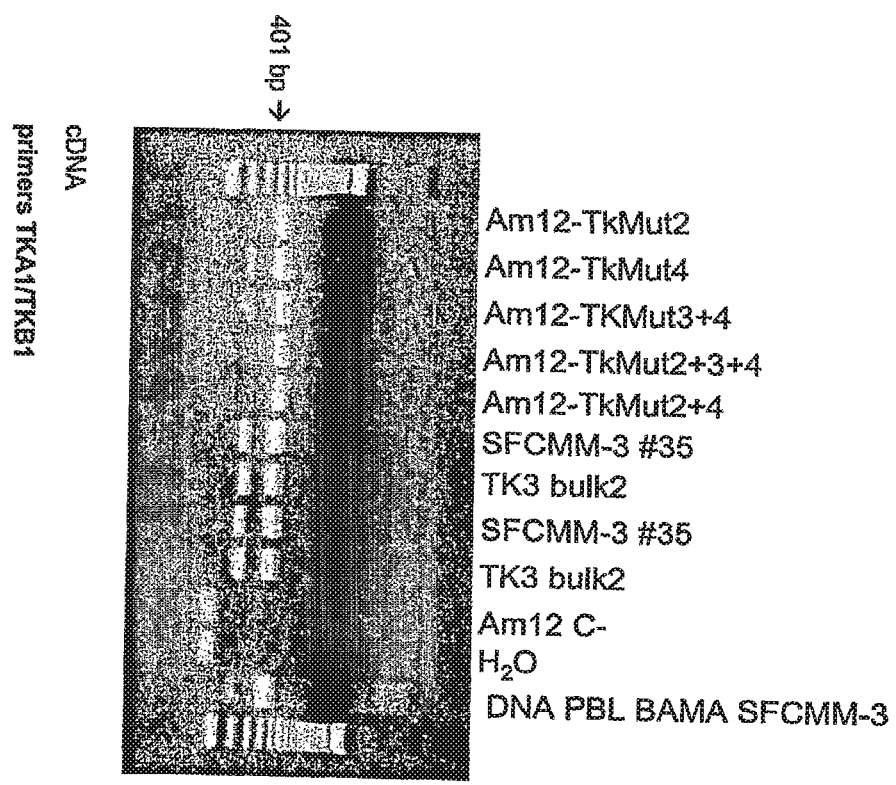
FIG. 8 shows HSV-tk. PCR product of cDNA derived from supernatants of Am12 cultures which has been transduced with the supernatants collected from the E86 cultures described in FIG. 7.

The unspliced form of HSV-tk is detected in all the samples except the negative controls (supernatant from non infected cells, Am12 C-, and $H_2O$) (FIG. 8). A lower band is detected in TkMut4 (mutation 4) and TkMut34 (mutations 3+4) mutants, corresponding to the lower band of TK3 and SFCMM-3 sample, respectively. The intensity of ethidium bromide signal is lower compared to TK3 and SFCMM-3, indicating that the spliced product is less represented in the mutants. This hand is not detected in TkMut2 (mutation 2), TkMut234 (mutations 2+3+4) and TkMut24 (mutations 2+4) mutants. Indeed, two very weak bands of approximately 100 and 200 bp are detected in TkMut2, TkMut234 and TkMut24 mutants.

Splicing Properties of HSV-tk Mutants in Transduced CEM A301 Cells and PBLs

Figure 9:
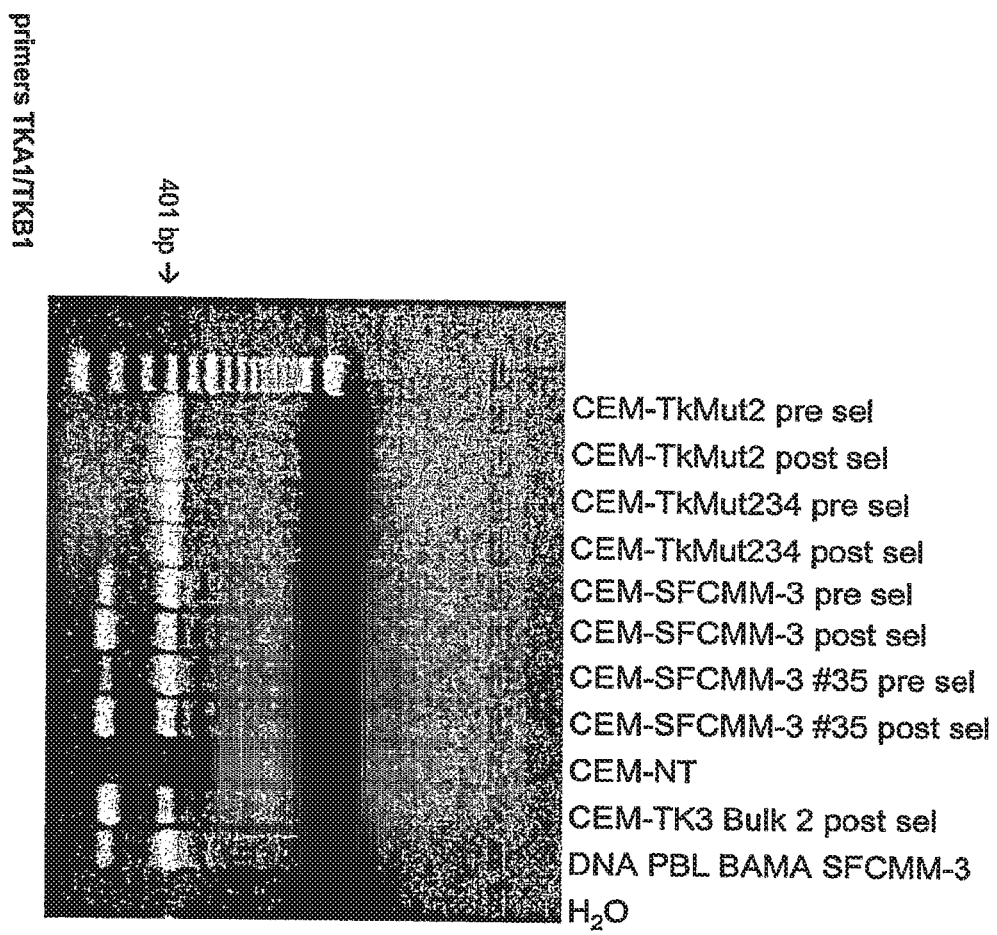
FIG. 9 shows TKA1/TKB1 HSV-tk PCR product of DNA derived from CEM A301 cells transduced with the supernatants collected from the Am12 cultures described in FIG. 8.

Genomic DNA from CEM A301 transduced with TkMut2 and TkMut234 mutants as well as with SFCMM-3 and TK3 supernatants was analyzed by PCR using TKA1/TKB1 primers. The unspliced form of HSV-tk (401 bp) is detected in all the samples except the negative controls (non transduced cells, CEM NT, and $H_2O$) (FIG. 9). A lower band is detected in TK3 and SFCMM-3 preselection and postselection sample, corresponding to the spliced form of HSV-tk gene. No lower band is observed in CEM transduced with TkMut2 and TkMut234 mutants, before and after selection.

To exclude the possibility of alternative splicing events occurring in different regions of HSV-tk gene, a more extensive analysis of CEM A301 transduced with TkMut2 as well as with SFCMM-3 supernatants was done using TKY1/TKY2 and TKZ1/TKZ2 primers.

Figure 10:
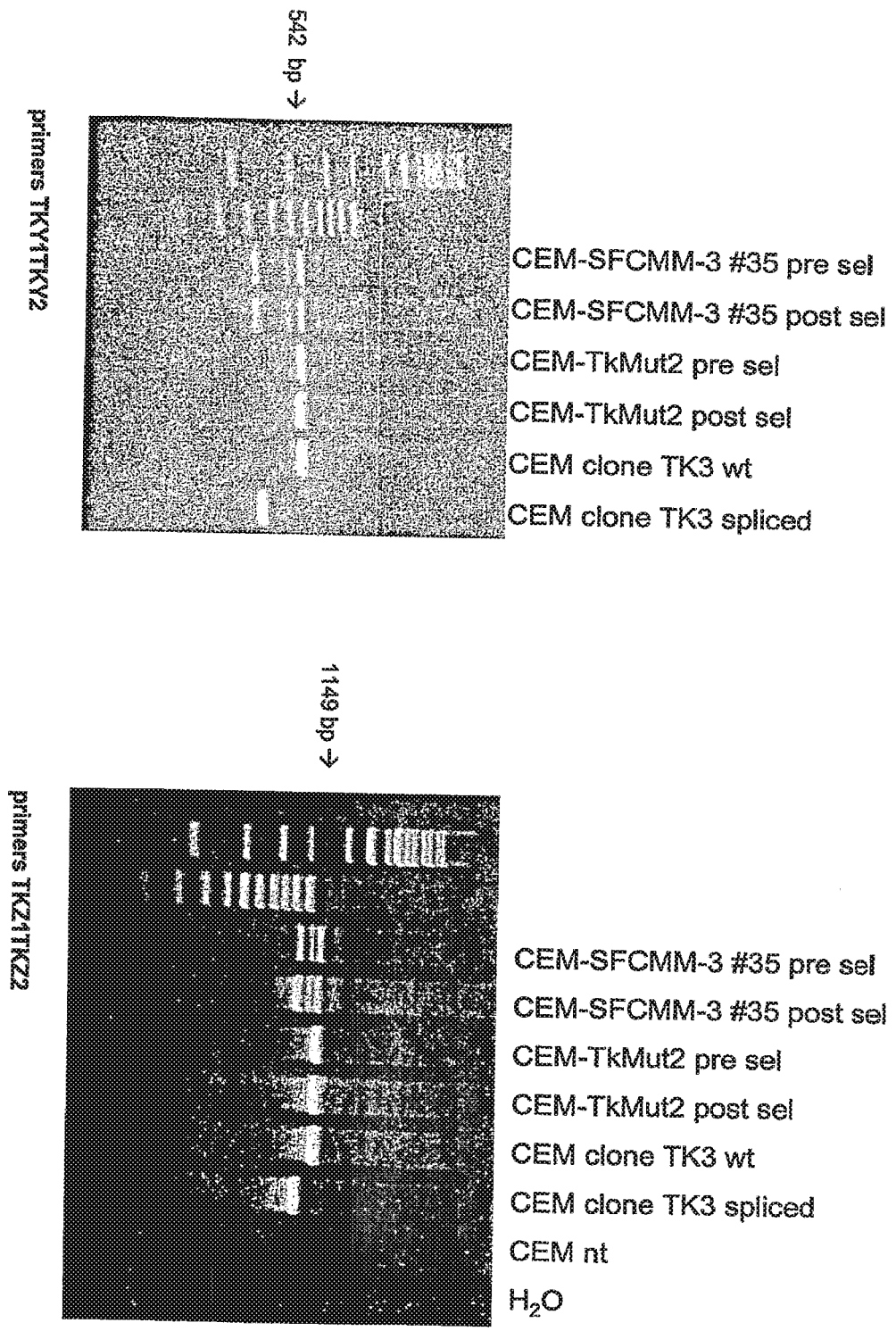
FIG. 10 shows TKY1/TKY2 and TKZ1/TKZ2 HSV-tk PCR products of DNA derived from CEM A301 cells transduced with the supernatants collected from the Am12 cultures described in FIG. 8.

The unspliced form of HSV-tk (542 bp and 1149 bp, respectively) is detected in all the samples (FIG. 10). A lower band is detected in SFCMM-3 preselection and post-selection sample, corresponding to the spliced form of HSV-tk gene. No lower band is observed in CEM transduced with TkMut2, nor with TKY1/TKY2 neither with TKZ1/TKZ2 PCR primers.

Figure 11:
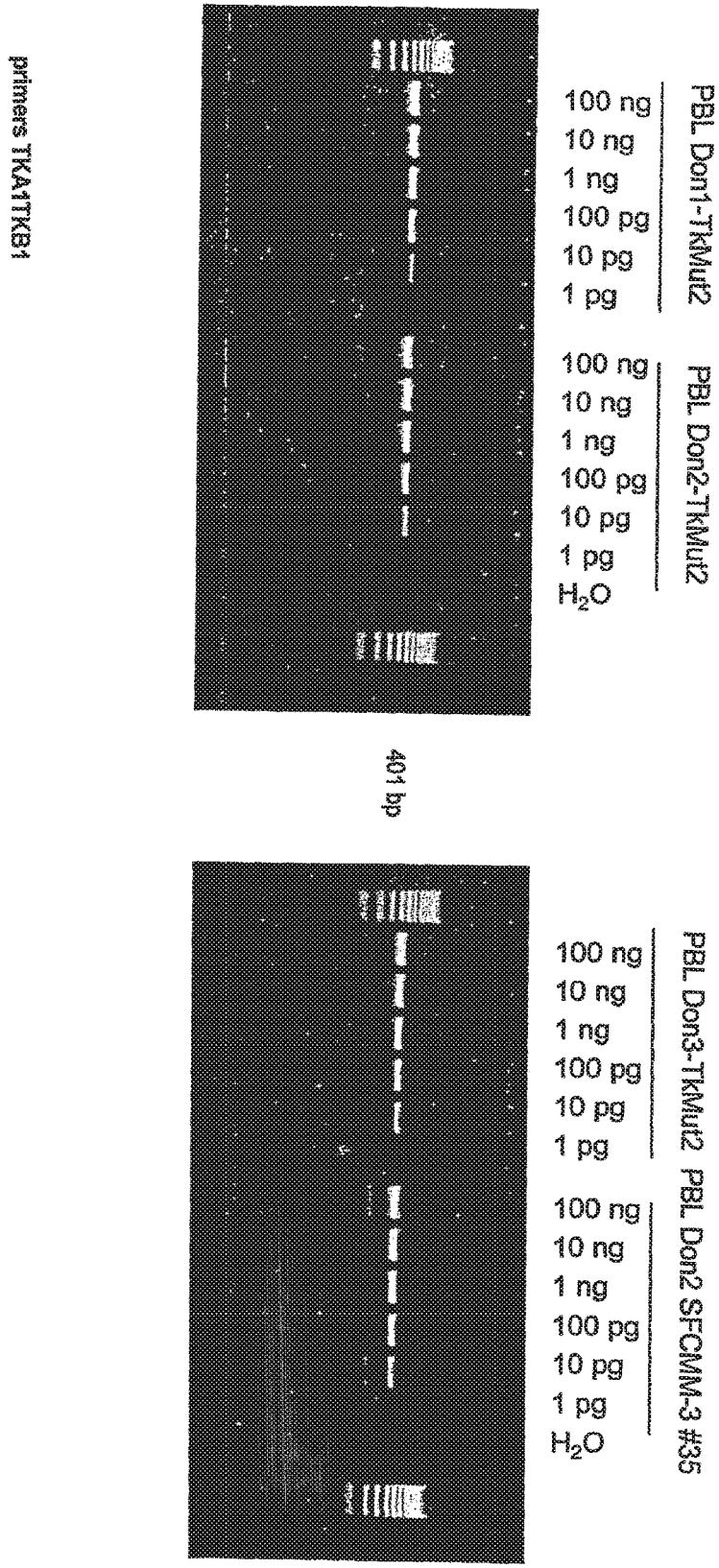
FIG. 11 shows TKA1/TKB1 HSV-tk PCR product of DNA derived from PBLs transduced with the supernatants collected from the Am12 cultures described in FIG. 8.
Figure 12:
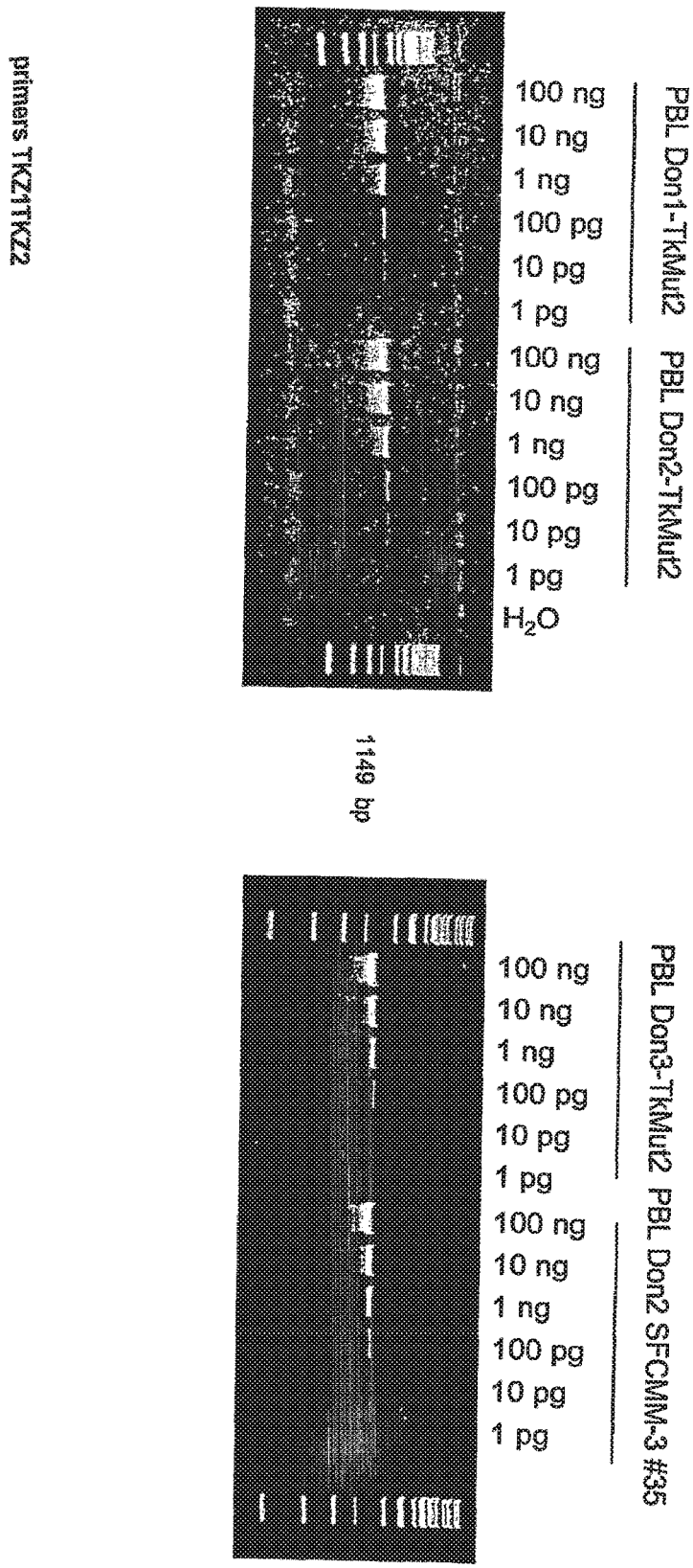
FIG. 12 shows TKZ1/TKZ2 HSV-tk PCR product of DNA derived from PBLs transduced with the supernatants collected from the Am12 cultures described in FIG. 8.

Genomic DNA from PBLs of three different donors (Don1, Don2, Don3) transduced with SFCMM-3 and/or TkMut2 supernatants was analyzed by PCR using TKA1/TKB1 primers. The =spliced form of HSV-tk (401 bp) is detected in all the samples (FIG. 11). A lower band is detected in SFCMM-3 sample, corresponding to the spliced form of HSV-tk gene. No lower band is observed in PBLs transduced with TkMut2. The same result was obtained using TKZ1/TKZ2 primers (FIG. 12), which encompasses the full-length HSV-tk gene (1149 bp), thus excluding the possibility that the introduced mutation could generated different splicing variants.

Overall these findings indicate that the introduced mutations abolish or at least very significantly decrease any HSV-tk gene spliced form in transduced CEM as well as in transduced lymphocytes.

TABLE 1

Analysis of HSV-tk spliced form on SFCMM-3 supernatants and transduced PBLs

| SFCMM-3 vector supernatant Lot number | % Spliced HSV-tk/Unspliced HSV-tk + Spliced HSV-tk | |
|---|---|---|
| | RNA (supernatant) | DNA (transduced PBLs) |
| 50.302-22 | 0.65 | 0.84 |
| | | 1.25 |
| 50.302-23 | 0.65 | 1.50 |
| 50.302-24 | 0.98 | 1.58 |
| 50.302-26 | 0.72 | 1.00 |
| | | 0.92 |
| | | 2.02 |
| 02/047 | 1.10 | 3.86 |
| 03/087 | 2.60 | 4.00 |
| mean | 1.12 | 1.89 |
| sd | 0.75 | 1.22 |
| n | 6 | 9 |
| min | 0.65 | 0.84 |
| max | 2.60 | 4.00 |

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Moolten, Cancer Res. 46, p 5276 (1986)
Mullen, Pharmac. Ther. 63, p 199 (1994)
Marini et al., Gene Therapy 2, p 655 (1995)
Kokoris et al., Gene Therapy 6, p 1415-1426 (1999)
Fillat et al., Current. Gene Therapy 3, p 13 2003
Tiberghien et al., Blood 97, p 63 (2001)
Garin et al., Blood 97, p 122 (2001)
Chalmers, Molecular Therapy 4 p 146 (2001)
Rettig et al., Molecular Therapy 8, p 29 (2003)
McKnight et al., Nuc, Acids Res 8, p 5949 (1980)
Swain and Galloway, J. Virol. 46, p 1045 (1983)
Davidson and Scott, J. Gen. Virol. 67, p 1759 (1986)
Otsuka and Kit, Virology 135, p 316-330, (1984)
Nunberg et al., J. Virol. 63 p 3240 (1989)
Robertson and Whalley, Nuc. Acids Res. 16 p 11303 (1988)
Mittal and Field, J. Virol 70 p 2901 (1989)
Martin et al., J Virol. 63 p 2847 (1989)
Scott et al., J Gen. Virol. 70 p 3055 (1989)
Honess et al., J. Gen. Virol. 70 p 3003 (1989)
Baer et al., Nature (London) 310 p 207 (1984)
McKnight et al., Nucl. Acids Res, 8 p 5949 (1980)
Drinkwater and Klinedinst, PNAS 83 p 3402 (1986)
Liao and Wise Gene 88 p 107 (1990)
Horwitz et al., Genome 3 p 112 (1989)
Lewis et al., EMBO. J 11 p 3053 (1992)
Lewis and Emerman J. Virol, 68 p 510 (1994)
Meyer, et al., J Gen. Virol. 72 p 1031 (1991)
Smith and Moss Gene, 25 p 21 (1983)
Upton, et al., J. Virology 60 p 920 (1986)
Gershon, et al., J. Gen. Virol. 70 p 525 (1989)
Weir, et al., J. Virol. 46 p 530 (1983)
Esposito, et al., Virology 135 p 561 (1984)
Hruby, et al., PNAS, 80 p 3411 (1983)
Kilpatrick, et al., Virology 143 p 399 (1985)
Binns, et al., J. Gen. Virol 69 p 1275 (1988)
Boyle, et al., Virology 156 p 355 (1987)
Schnitzlein, et al., J. Virological Method, 20 p 341 (1988)
Lytvyn, et al., J Gen. Virol. 73 p 3235 (1992)
Moss Science 252 p 1662 (1991)
Verzeletti, Hum. Gene Therapy 9 p 2243 (1998)
Chalmers, Mol. Therapy 4 p 146 (2001)

The invention claimed is:

1. A method of destroying cells comprising (i) introducing into said cells a polynucleotide selected from the group consisting of the TkMut23 polynucleotide as set forth in SEQ ID NO:3, the TkMut24 polynucleotide as set forth in SEQ ID NO:4, and the TkMut234 polynucleotide as set forth in SEQ ID NO:7, and expressing the thymidine kinase encoded by the polynucleotide in said cells; and (ii) simultaneously, separately or sequentially contacting said cells with a non-toxic agent which is converted by the thymidine kinase to a toxic agent, thereby destroying the cells.

2. The method according to claim 1, wherein the non-toxic agent is selected from the group consisting of ganciclovir, acyclovir, triflurothymidine, 1-[2-deoxy, 2-fluoro, β-D-arabino furanosyl]-5-iodouracil, ara-A, ara 1, 1-β-D arabino furanosyl thymine, 5-ethyl-2'deoxyuridine, 5-iodo-5'-amino-2,5'-dideoxyuridine, idoxuridine, AZT, AIV, dideoxycytidine, Ara C, and bromovinyl deoxyuridine (BVDU).

3. A method of treating a patient with cells in need of destruction comprising (i) introducing into the patient a polynucleotide selected from the group consisting of the TkMut23 polynucleotide as set forth in SEQ ID NO:3, the TkMut24 polynucleotide as set forth in SEQ ID NO:4, and the TkMut234 polynucleotide as set forth in SEQ ID NO:7, and expressing the thymidine kinase encoded by the polynucleotide in said cells; and (ii) simultaneously, separately or sequentially introducing into the patient a non-toxic agent which is converted by the thymidine kinase to a toxic agent, thereby destroying the cells and treating said patient.

4. The method according to claim 3, wherein the non-toxic agent is selected from the group consisting of ganciclovir, acyclovir, triflurothymidine, 1-[2-deoxy, 2-fluoro, β-D-arabino furanosyl]-5-iodouracil, ara-A, ara 1, 1-β-D arabino furanosyl thymine, 5-ethyl-2'deoxyuridine, 5-iodo-5'-amino-2,5'-dideoxyuridine, idoxuridine, AZT, AIV, dideoxycytidine, Ara C, and bromovinyl deoxyuridine (BVDU).

5. A method of treating a patient with cells in need of destruction comprising (i) removing the cells from the patient or donor cells; (ii) introducing into the cells ex vivo a polynucleotide selected from the group consisting of the TkMut23 polynucleotide as set forth in SEQ ID NO:3, the TkMut24 polynucleotide as set forth in SEQ ID NO:4, and the TkMut234 polynucleotide as set forth in SEQ ID NO:7; (iii) introducing the modified cells into the patient; (iv) allowing the cells to express the thymidine kinase encoded by the polynucleotide; and (v) administering to the patient a non-toxic agent which is converted by the thymidine kinase into a toxic agent, thereby destroying the cells and treating said patient.

6. The method according to claim 5, wherein the non-toxic agent is selected from the group consisting of ganciclovir, acyclovir, triflurothymidine, 1-[2-deoxy, 2-fluoro, β-D-arabino furanosyl]-5-iodouracil, ara-A, ara 1, 1-β-D arabino furanosyl thymine, 5-ethyl-2'deoxyuridine, 5-iodo-5'-amino-2,5'-dideoxyuridine, idoxuridine, AZT, AIV, dideoxycytidine, Ara C, and bromovinyl deoxyuridine (BVDU).

7. A method of treating graft-versus-host disease in a patient comprising: (i) administering to the patient T-cells genetically engineered to include a polynucleotide selected from the group consisting of the TkMut23 polynucleotide as set forth in SEQ ID NO:3, the TkMut24 polynucleotide as set forth in SEQ ID NO:4, and the TkMut234 polynucleotide as set forth in SEQ ID NO:7, and expressing the thymidine kinase encoded by the polynucleotide in said T-cells; and (ii) administering to said patient, on occurrence of graft-versus-host disease, a non-toxic agent which is converted by the thymidine kinase to a toxic agent thereby killing said genetically engineered T-cells and treating the graft-versus-host disease in said patient.

8. The method according to claim 7, wherein the non-toxic agent is selected from the group consisting of ganciclovir, acyclovir, triflurothymidine, 1-[2-deoxy, 2-fluoro, β-D-arabino furanosyl]-5-iodouracil, ara-A, ara 1, 1-β-D arabino furanosyl thymine, 5-ethyl-2'deoxyuridine, 5-iodo-5'-amino-2,5'-dideoxyuridine, idoxuridine, AZT, AIV, dideoxycytidine, Ara C, and bromovinyl deoxyuridine (BVDU).

* * * * *

SEQUENCE LISTING

```
<160> NUMBER OF SEQ ID NOS: 36

<210> SEQ ID NO 1
<211> LENGTH: 1131
<212> TYPE: DNA
<213> ORGANISM: Herpes simplex virus type 1

<400> SEQUENCE: 1
atggcttcgt accctgcca tcaacacgcg tctgcgttcg accaggctgc gcgttctcgc      60
ggccatagca accgacgtac ggcgttgcgc cctcgccggc agcaagaagc cacggaagtc     120
cgcctggagc agaaaatgcc cacgctactg cgggtttata tagacggtcc tcacgggatg     180
gggaaaacca ccaccacgca actgctggtg gccctgggtt cgcgcgacga tatcgtctac     240
gtacccgagc cgatgactta ctggcaggtg ctgggggctt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatgtcg gggggaggc tgggagttca catgccccgc ccccggccct caccctcatc     480
ttcgaccgcc atcccatcgc cgcccctcctg tgctacccgg ccgcgcgata ccttatgggc     540
agcatgaccc cccaggccgt gctggcgttc gtggccctca tcccgccgac cttgcccggc     600
```

```
acaaacatcg tgttgggggc ccttccggag acagacaca tcgaccgcct ggccaaacgc      660
cagcgccccg gcgagcggct tgacctggct atgctggccg cgattcgccg cgtttacggg      720
ctgcttgcca atacggtgcg gtatctgcag ggcggcgggt cgtggtggga ggattgggga      780
cagctttcgg ggacggccgt gccgccccag ggtgccgagc cccagagcaa cgcgggccca      840
cgaccccata tcgggacac gttatttacc ctgtttcggg ccccgagtt gctggccccc      900 aacggcgacc tgtataacgt gtttgcctgg gccttggaca tcttggccaa acgcctccgt      960
cccatgcacg tctttatcct ggattacgac caatcgcccg ccggctgccg ggacgccctg     1020
ctgcaactta cctccgggat ggtccagacc cacgtcacca ccccaggctc cataccgacg     1080
atctgcgacc tggcgcgcac gtttgcccgg gagatggggg aggctaactg a              1131

<210> SEQ ID NO 2
<211> LENGTH: 1131
<212> TYPE: DNA
<213> ORGANISM: Artificial
<220> FEATURE:
<223> OTHER INFORMATION: HSV-1 thymidine kinase mutant sequence.

<400> SEQUENCE: 2
atggcttcgt accccctgcca tcaacacgcg tctgcgttcg accaggctgc gcgttctcgc       60
ggccatagca accgacgtac ggcgttgcgc cctcgccggc agcaagaagc cacggaagtc      120
cgcctggagc agaaaatgcc cacgctactg cgggtttata tagacggtcc tcacgggatg      180
gggaaaacca ccaccacgca actgctggtg gccctgggtt cgcgcgacga tatcgtctac      240
gtacccgagc cgatgactta ctggcaggtg ctgggggctt ccgagacaat cgcgaacatc      300
tacaccacac aacaccgcct cgaccagggc gagatatcgg ccggggacgc ggcggtggta      360
atgacaagcg cccagataac aatgggcatg ccttatgccg tgaccgacgc cgttctggct      420
cctcatgtcg gggggaggc tgggagttca catgcccccgc ccccggccct caccctcatc      480
ttcgaccgcc atcccatcgc cgccctcctg tgctacccgg ccgcgcgata ccttatgggc      540
agcatgaccc ccaggccgt gctggcgttc gtggccctca tcccgccgac cttgccggc      600 acaaacatcg tgttgggggc ccttccggag acagacaca tcgaccgcct ggccaaacgc      660
cagcgccccg gcgagcggct tgacctggct atgctggccg cgattcgccg cgtttacggg      720
ctgcttgcca atacggtgcg gtatctgcag ggcggcgggt cgtggtggga ggattgggga      780
cagctttcgg ggacggccgt gccgccccag ggtgccgagc cccagagcaa cgcgggccca      840
cgaccccata tcgggacac gttatttacc ctgtttcggg ccccgagtt gctggccccc      900 aacggcgacc tgtataacgt gtttgcctgg gccttggacg tcttggccaa acgcctccgt      960
cccatgcacg tctttatcct ggattacgac caatcgcccg ccggctgccg ggacgccctg     1020
ctgcaactta cctccgggat ggtccagacc cacgtcacca ccccaggctc cataccgacg     1080
atctgcgacc tggcgcgcac gtttgcccgg gagatggggg aggctaactg a              1131

<210> SEQ ID NO 3
<211> LENGTH: 1131
<212> TYPE: DNA
<213> ORGANISM: Artificial
<220> FEATURE:
<223> OTHER INFORMATION: HSV-1 thymidine kinase mutant sequence.

<400> SEQUENCE: 3
atggcttcgt accccctgcca tcaacacgcg tctgcgttcg accaggctgc gcgttctcgc       60
```

```
ggccatagca accgacgtac ggcgttgcgc cctcgccggc agcaagaagc cacggaagtc    120
cgcctggagc agaaaatgcc cacgctactg cgggtttata tagacggtcc tcacgggatg    180
gggaaaacca ccaccacgca actgctggtg gccctgggtt cgcgcgacga tatcgtctac    240
gtacccgagc cgatgactta ctggcaggtg ctgggggctt ccgagacaat cgcgaacatc    300
tacaccacac aacaccgcct cgaccagggc gagatatcgg ccggggacgc ggcggtggta    360
atgacaagcg cccagataac aatgggcatg ccttatgccg tgaccgacgc cgttctggct    420
cctcatgtcg ggggggaggc tgggagttca catgccccgc ccccggccct caccctcatc    480
ttcgaccgcc atcccatcgc cgccctcctg tgctacccgg ccgcgcgata ccttatgggc    540
tccatgaccc cccaggccgt gctggcgttc gtggccctca tcccgccgac cttgccggc    600
acaaacatcg tgttggggc ccttccggag acagacaca tcgaccgcct ggccaaacgc    660
cagcgccccg gcgagcggct tgacctggct atgctggccg cgattcgccg cgtttacggg    720
ctgcttgcca atacggtgcg gtatctgcag ggcggcgggt cgtggtggga ggattgggga    780
cagctttcgg ggacggccgt gccgcccag ggtgccgagc ccagagcaa cgcgggccca    840
cgaccccata tcggggacac gttatttacc ctgtttcggg ccccgagtt gctggccccc    900
aacggcgacc tgtataacgt gtttgcctgg gccttggacg tcttggccaa cgcctccgt    960
cccatgcacg tctttatcct ggattacgac caatcgcccg ccggctgccg ggacgccctg   1020
ctgcaactta cctccgggat ggtccagacc cacgtcacca ccccaggctc cataccgacg   1080
atctgcgacc tggcgcgcac gtttgcccgg gagatggggg aggctaactg a            1131
```

<210> SEQ ID NO 4
<211> LENGTH: 1131
<212> TYPE: DNA
<213> ORGANISM: Artificial
<220> FEATURE:
<223> OTHER INFORMATION: HSV-1 thymidine kinase mutant sequence.

<400> SEQUENCE: 4

```
atggcttcgt accccctgcca tcaacacgcg tctgcgttcg accaggctgc gcgttctcgc     60
ggccatagca accgacgtac ggcgttgcgc cctcgccggc agcaagaagc cacggaagtc    120
cgcctggagc agaaaatgcc cacgctactg cgggtttata tagacggtcc tcacgggatg    180
gggaaaacca ccaccacgca actgctggtg gccctgggtt cgcgcgacga tatcgtctac    240
gtacccgagc cgatgactta ctggcaggtg ctgggggctt ccgagacaat cgcgaacatc    300
tacaccacac aacaccgcct cgaccagggc gagatatcgg ccggggacgc ggcggtggta    360
atgacaagcg cccagataac aatgggcatg ccttatgccg tgaccgacgc cgttctggct    420
cctcatgtcg ggggggaggc tgggagttca catgccccgc ccccggccct caccctcatc    480
ttcgaccgcc atcccatcgc cgccctcctg tgctacccgg ccgcgcgata ccttatgggc    540
agcatgaccc cccaagccgt gctggcgttc gtggccctca tcccgccgac cttgccggc    600
acaaacatcg tgttggggc ccttccggag acagacaca tcgaccgcct ggccaaacgc    660
cagcgccccg gcgagcggct tgacctggct atgctggccg cgattcgccg cgtttacggg    720
ctgcttgcca atacggtgcg gtatctgcag ggcggcgggt cgtggtggga ggattgggga    780
cagctttcgg ggacggccgt gccgcccag ggtgccgagc ccagagcaa cgcgggccca    840
cgaccccata tcggggacac gttatttacc ctgtttcggg ccccgagtt gctggccccc    900
aacggcgacc tgtataacgt gtttgcctgg gccttggacg tcttggccaa cgcctccgt    960
cccatgcacg tctttatcct ggattacgac caatcgcccg ccggctgccg ggacgccctg   1020
```
ctgcaactta cctccgggat ggtccagacc cacgtcacca ccccaggctc cataccgacg    1080
atctgcgacc tggcgcgcac gtttgcccgg gagatggggg aggctaactg a              1131

<210> SEQ ID NO 5
<211> LENGTH: 1131
<212> TYPE: DNA
<213> ORGANISM: Artificial
<220> FEATURE:
<223> OTHER INFORMATION: HSV-1 thymidine kinase mutant sequence.

<400> SEQUENCE: 5
atggcttcgt acccctgcca tcaacacgcg tctgcgttcg accaggctgc gcgttctcgc     60
ggccatagca accgacgtac ggcgttgcgc cctcgccggc agcaagaagc cacggaagtc    120
cgcctggagc agaaaatgcc cacgctactg cgggtttata tagacggtcc tcacgggatg    180
gggaaaacca ccaccacgca actgctggtg gccctgggtt cgcgcgacga tatcgtctac    240
gtacccgagc cgatgactta ctggcaggtg ctggggctt ccgagacaat cgcgaacatc    300
tacaccacac aacaccgcct cgaccagggt gagatatcgg ccggggacgc ggcggtggta    360
atgacaagcg cccagataac aatgggcatg cctatgccg tgaccgacgc cgttctggct    420
cctcatgtcg ggggggaggc tgggagttca catgccccgc cccggccct caccctcatc    480 ttcgaccgcc atcccatcgc cgccctcctg tgctacccgg ccgcgcgata ccttatgggc    540
tccatgaccc cccaagccgt gctggcgttc gtggccctca tcccgccgac cttgccggc    600 acaaacatct gttggggc cttccggag acagacaca tcgaccgcct ggccaaacgc    660
cagcgccccg cgagcggct tgacctggct atgctggccg cgattcgccg cgtttacggg    720
ctgcttgcca atacggtgcg gtatctgcag ggcggcgggt cgtggtggga ggattgggga    780
cagctttcgg gacggccgt gccgcccag ggtgccgagc ccagagcaa cgcgggccca    840 cgaccccata tcggggacac gttatttacc ctgtttcggg ccccgagtt gctggccccc    900 aacggcgacc tgtataacgt gtttgcctgg gccttggacg tcttggccaa cgcctccgt    960 cccatgcacg tctttatcct ggattacgac caatcgcccg ccggctgccg ggacgccctg   1020
ctgcaactta cctccgggat ggtccagacc cacgtcacca ccccaggctc cataccgacg   1080
atctgcgacc tggcgcgcac gtttgcccgg gagatggggg aggctaactg a             1131

<210> SEQ ID NO 6
<211> LENGTH: 1131
<212> TYPE: DNA
<213> ORGANISM: Artificial
<220> FEATURE:
<223> OTHER INFORMATION: HSV-1 thymidine kinase mutant sequence.

<400> SEQUENCE: 6
atggcttcgt acccctgcca tcaacacgcg tctgcgttcg accaggctgc gcgttctcgc     60
ggccatagca accgacgtac ggcgttgcgc cctcgccggc agcaagaagc cacggaagtc    120
cgcctggagc agaaaatgcc cacgctactg cgggtttata tagacggtcc tcacgggatg    180
gggaaaacca ccaccacgca actgctggtg gccctgggtt cgcgcgacga tatcgtctac    240
gtacccgagc cgatgactta ctggcaggtg ctggggctt ccgagacaat cgcgaacatc    300
tacaccacac aacaccgcct cgaccagggt gagatatcgg ccggggacgc ggcggtggta    360
atgacaagcg cccagataac aatgggcatg cctatgccg tgaccgacgc cgttctggct    420
cctcatgtcg ggggggaggc tgggagttca catgccccgc cccggccct caccctcatc    480

| | |
|---|---|
| ttcgaccgcc atcccatcgc cgccctcctg tgctacccgg ccgcgcgata ccttatgggc | 540 |
| agcatgaccc cccaagccgt gctggcgttc gtggccctca tcccgccgac cttgcccggc | 600 |
| acaaacatcg tgttgggggc ccttccggag acagacaca tcgaccgcct ggccaaacgc | 660 |
| cagcgccccg gcgagcggct tgacctggct atgctggccg cgattcgccg cgtttacggg | 720 |
| ctgcttgcca atacggtgcg gtatctgcag ggcggcgggt cgtggtggga ggattgggga | 780 |
| cagctttcgg ggacggccgt gccgcccag ggtgccgagc cccagagcaa cgcgggccca | 840 |
| cgaccccata tcggggacac gttatttacc ctgtttcggg ccccgagtt gctggccccc | 900 |
| aacggcgacc tgtataacgt gtttgcctgg gccttggacg tcttggccaa acgcctccgt | 960 |
| cccatgcacg tctttatcct ggattacgac caatcgcccg ccggctgccg ggacgccctg | 1020 |
| ctgcaactta cctccgggat ggtccagacc cacgtcacca ccccaggctc cataccgacg | 1080 |
| atctgcgacc tggcgcgcac gtttgcccgg gagatggggg aggctaactg a | 1131 |

<210> SEQ ID NO 7
<211> LENGTH: 1131
<212> TYPE: DNA
<213> ORGANISM: Artificial
<220> FEATURE:
<223> OTHER INFORMATION: HSV-1 thymidine kinase mutant sequence.

<400> SEQUENCE: 7

| | |
|---|---|
| atggcttcgt acccctgcca tcaacacgcg tctgcgttcg accaggctgc gcgttctcgc | 60 |
| ggccatagca accgacgtac ggcgttgcgc cctcgccggc agcaagaagc cacggaagtc | 120 |
| cgcctggagc agaaaatgcc cacgctactg cgggtttata tagacggtcc tcacgggatg | 180 |
| gggaaaacca ccaccacgca actgctggtg gccctgggtt cgcgcgacga tatcgtctac | 240 |
| gtacccgagc cgatgactta ctggcaggtg ctgggggctt ccgagacaat cgcgaacatc | 300 |
| tacaccacac aacaccgcct cgaccagggc gagatatcgg ccggggacgc ggcggtggta | 360 |
| atgacaagcg cccagataac aatgggcatg ccttatgccg tgaccgacgc cgttctggct | 420 |
| cctcatgtcg gggggaggc tgggagttca catgccccgc cccggccct caccctcatc | 480 |
| ttcgaccgcc atcccatcgc cgccctcctg tgctacccgg ccgcgcgata ccttatgggc | 540 |
| tccatgaccc cccaagccgt gctggcgttc gtggccctca tcccgccgac cttgcccggc | 600 |
| acaaacatcg tgttgggggc ccttccggag acagacaca tcgaccgcct ggccaaacgc | 660 |
| cagcgccccg gcgagcggct tgacctggct atgctggccg cgattcgccg cgtttacggg | 720 |
| ctgcttgcca atacggtgcg gtatctgcag ggcggcgggt cgtggtggga ggattgggga | 780 |
| cagctttcgg ggacggccgt gccgcccag ggtgccgagc cccagagcaa cgcgggccca | 840 |
| cgaccccata tcggggacac gttatttacc ctgtttcggg ccccgagtt gctggccccc | 900 |
| aacggcgacc tgtataacgt gtttgcctgg gccttggacg tcttggccaa acgcctccgt | 960 |
| cccatgcacg tctttatcct ggattacgac caatcgcccg ccggctgccg ggacgccctg | 1020 |
| ctgcaactta cctccgggat ggtccagacc cacgtcacca ccccaggctc cataccgacg | 1080 |
| atctgcgacc tggcgcgcac gtttgcccgg gagatggggg aggctaactg a | 1131 |

<210> SEQ ID NO 8
<211> LENGTH: 300
<212> TYPE: DNA
<213> ORGANISM: Artificial
<220> FEATURE:
<223> OTHER INFORMATION: HSV-tk gene sequences in vector SFCMM-3.

<400> SEQUENCE: 8

```
ccgcctcgac caggtgaga tatcggccgg ggacgcggcg gtggtaatga caagcgccca    60
gataacaatg gcatgcctt atgccgtgac cgacgccgtt ctggctcctc atgtcggggg   120
ggaggctggg agttcacatg ccccgccccc ggccctcacc ctcatcttcg accgccatcc   180
catcgccgcc ctcctgtgct acccggccgc gcgataccctt atgggcagca tgacccccca   240
ggccgtgctg gcgttcgtgg ccctcatccc gccgaccttg ccggcacaa acatcgtgtt   300
```

<210> SEQ ID NO 9
<211> LENGTH: 300
<212> TYPE: DNA
<213> ORGANISM: Artificial
<220> FEATURE:
<223> OTHER INFORMATION: HSV-tk sequences in vector TK3.

<400> SEQUENCE: 9

```
ccgcctcgac caaggtgaga tatcggccgg ggacgcggcg gtggtaatga caagcgccca    60
gataacaatg gcatgcctt atgccgtgac cgacgccgtt ctggctcctc atgtcggggg   120
ggaggctggg agttcacatg ccccgccccc ggccctcacc ctcatcttcg accgccatcc   180
catcgccgcc ctcctgtgct acccggccgc gcgataccctt atgggcagca tgacccccca   240
agccgtgctg gcgttcgtgg ccctcatccc gccgaccttg ccggcacaa acatcgtgtt   300
```

<210> SEQ ID NO 10
<211> LENGTH: 15
<212> TYPE: DNA
<213> ORGANISM: Artificial
<220> FEATURE:
<223> OTHER INFORMATION: Mutations introduced in the SFCMM-3 vector.

<400> SEQUENCE: 10

```
ctcgaccagg gtgag                                                    15
```

<210> SEQ ID NO 11
<211> LENGTH: 5
<212> TYPE: PRT
<213> ORGANISM: Artificial
<220> FEATURE:
<223> OTHER INFORMATION: Mutations introduced in the SFCMM-3 vector.

<400> SEQUENCE: 11

Leu Asp Gln Gly Glu
1               5

<210> SEQ ID NO 12
<211> LENGTH: 24
<212> TYPE: DNA
<213> ORGANISM: Artificial
<220> FEATURE:
<223> OTHER INFORMATION: Mutations introduced in the SFCMM-3 vector.

<400> SEQUENCE: 12

```
atgggcagca tgacccccca ggcc                                          24
```

<210> SEQ ID NO 13
<211> LENGTH: 8
<212> TYPE: PRT
<213> ORGANISM: Artificial
<220> FEATURE:
<223> OTHER INFORMATION: Mutations introduced in the SFCMM-3 vector.

<400> SEQUENCE: 13

Met Gly Ser Met Thr Pro Gln Ala

```
<210> SEQ ID NO 14
<211> LENGTH: 19
<212> TYPE: DNA
<213> ORGANISM: Artificial
<220> FEATURE:
<223> OTHER INFORMATION: Oligonucleotide primer.

<400> SEQUENCE: 14
cggcggtggt aatgacaag                                                  19

<210> SEQ ID NO 15
<211> LENGTH: 17
<212> TYPE: DNA
<213> ORGANISM: Artificial
<220> FEATURE:
<223> OTHER INFORMATION: Oligonucleotide primer.

<400> SEQUENCE: 15
gcgtcggtca cggcata                                                    17

<210> SEQ ID NO 16
<211> LENGTH: 16
<212> TYPE: DNA
<213> ORGANISM: Artificial
<220> FEATURE:
<223> OTHER INFORMATION: Oligonucleotide probe.

<400> SEQUENCE: 16
ccagataaca atgggc                                                     16

<210> SEQ ID NO 17
<211> LENGTH: 16
<212> TYPE: DNA
<213> ORGANISM: Artificial
<220> FEATURE:
<223> OTHER INFORMATION: Oligonucleotide primer.

<400> SEQUENCE: 17
ggatgagggc cacgaa                                                     16

<210> SEQ ID NO 18
<211> LENGTH: 22
<212> TYPE: DNA
<213> ORGANISM: Artificial
<220> FEATURE:
<223> OTHER INFORMATION: Oligonucleotide primer.

<400> SEQUENCE: 18
cgaacatcta caccacacaa ca                                              22

<210> SEQ ID NO 19
<211> LENGTH: 18
<212> TYPE: DNA
<213> ORGANISM: Artificial
<220> FEATURE:
<223> OTHER INFORMATION: Oligonucleotide probe.

<400> SEQUENCE: 19
ccagcacggc cctggtcg                                                   18

<210> SEQ ID NO 20
<211> LENGTH: 23
<212> TYPE: DNA
<213> ORGANISM: Artificial
```

```
<220> FEATURE:
<223> OTHER INFORMATION: Oligonucleotide primer.

<400> SEQUENCE: 20
ttctctaggc gccggaattc gtt                                              23

<210> SEQ ID NO 21
<211> LENGTH: 23
<212> TYPE: DNA
<213> ORGANISM: Artificial
<220> FEATURE:
<223> OTHER INFORMATION: Oligonucleotide primer.

<400> SEQUENCE: 21
atccaggata aagacgtgca tgg                                              23

<210> SEQ ID NO 22
<211> LENGTH: 20
<212> TYPE: DNA
<213> ORGANISM: Artificial
<220> FEATURE:
<223> OTHER INFORMATION: Oligonucleotide primer.

<400> SEQUENCE: 22
cgtacccgag ccgatgactt                                                  20

<210> SEQ ID NO 23
<211> LENGTH: 20
<212> TYPE: DNA
<213> ORGANISM: Artificial
<220> FEATURE:
<223> OTHER INFORMATION: Oligonucleotide primer.

<400> SEQUENCE: 23
tgtgtctgtc ctccggaagg                                                  20

<210> SEQ ID NO 24
<211> LENGTH: 19
<212> TYPE: DNA
<213> ORGANISM: Artificial
<220> FEATURE:
<223> OTHER INFORMATION: Oligonucleotide primer.

<400> SEQUENCE: 24
ccatagcaac cgacgtacg                                                   19

<210> SEQ ID NO 25
<211> LENGTH: 19
<212> TYPE: DNA
<213> ORGANISM: Artificial
<220> FEATURE:
<223> OTHER INFORMATION: Oligonucleotide primer.

<400> SEQUENCE: 25
gaatcgcggc cagcatagc                                                   19

<210> SEQ ID NO 26
<211> LENGTH: 22
<212> TYPE: DNA
<213> ORGANISM: Artificial
<220> FEATURE:
<223> OTHER INFORMATION: Oligonucleotide primer.

<400> SEQUENCE: 26
ttatatagac ggtcctcacg gg                                               22
```

```
<210> SEQ ID NO 27
<211> LENGTH: 20
<212> TYPE: DNA
<213> ORGANISM: Artificial
<220> FEATURE:
<223> OTHER INFORMATION: Oligonucleotide primer.

<400> SEQUENCE: 27
ccagcatagc caggtcaagc                                                  20

<210> SEQ ID NO 28
<211> LENGTH: 18
<212> TYPE: DNA
<213> ORGANISM: Artificial
<220> FEATURE:
<223> OTHER INFORMATION: Oligonucleotide primer.

<400> SEQUENCE: 28
gccaccatgg cttcgtac                                                    18

<210> SEQ ID NO 29
<211> LENGTH: 24
<212> TYPE: DNA
<213> ORGANISM: Artificial
<220> FEATURE:
<223> OTHER INFORMATION: Oligonucleotide primer.

<400> SEQUENCE: 29
cgagttaatt ctcagttagc ctcc                                             24

<210> SEQ ID NO 30
<211> LENGTH: 26
<212> TYPE: DNA
<213> ORGANISM: Artificial
<220> FEATURE:
<223> OTHER INFORMATION: Oligonucleotide primer.

<400> SEQUENCE: 30
cctcgaccag ggcgagatat cggccg                                           26

<210> SEQ ID NO 31
<211> LENGTH: 26
<212> TYPE: DNA
<213> ORGANISM: Artificial
<220> FEATURE:
<223> OTHER INFORMATION: Oligonucleotide primer.

<400> SEQUENCE: 31
cctcgaccag ggcgagatat cggccg                                           26

<210> SEQ ID NO 32
<211> LENGTH: 24
<212> TYPE: DNA
<213> ORGANISM: Artificial
<220> FEATURE:
<223> OTHER INFORMATION: Oligonucleotide primer.

<400> SEQUENCE: 32 atgaccccccc aagccgtgct ggcg                                            24

<210> SEQ ID NO 33
<211> LENGTH: 34
<212> TYPE: DNA
<213> ORGANISM: Artificial
<220> FEATURE:
<223> OTHER INFORMATION: Oligonucleotide primer.
```

-continued

```
<400> SEQUENCE: 33
taccttatgg gctccatgac cccccaagcc gtgc                               34

<210> SEQ ID NO 34
<211> LENGTH: 24
<212> TYPE: DNA
<213> ORGANISM: Artificial
<220> FEATURE:
<223> OTHER INFORMATION: Oligonucleotide primer.

<400> SEQUENCE: 34 atgaccccccc aagccgtgct ggcg                                         24

<210> SEQ ID NO 35
<211> LENGTH: 26
<212> TYPE: DNA
<213> ORGANISM: Artificial
<220> FEATURE:
<223> OTHER INFORMATION: Oligonucleotide primer.

<400> SEQUENCE: 35
cctcgaccag ggcgagatat cggccg                                        26

<210> SEQ ID NO 36
<211> LENGTH: 34
<212> TYPE: DNA
<213> ORGANISM: Artificial
<220> FEATURE:
<223> OTHER INFORMATION: Oligonucleotide primer.

<400> SEQUENCE: 36
taccttatgg gctccatgac cccccaagcc gtgc                               34
```